United States Patent [19]

Mortara et al.

[11] Patent Number: 5,704,351

[45] Date of Patent: Jan. 6, 1998

[54] MULTIPLE CHANNEL BIOMEDICAL DIGITAL TELEMETRY TRANSMITTER

[75] Inventors: David W. Mortara, River Hills; Brian E. Sueppel, Grafton, both of Wis.

[73] Assignee: Mortara Instrument, Inc., Milwaukee, Wis.

[21] Appl. No.: 396,151

[22] Filed: Feb. 28, 1995

[51] Int. Cl.$^6$ ............................................. A61N 5/00
[52] U.S. Cl. ................................. 128/630; 128/904
[58] Field of Search .............................. 128/903, 630, 128/696

[56] References Cited

U.S. PATENT DOCUMENTS

| | | | |
|---|---|---|---|
| 4,141,351 | 2/1979 | James et al. | 128/903 |
| 5,127,404 | 7/1992 | Wybomy et al. | 128/903 |
| 5,305,761 | 4/1994 | Byrne et al. | 128/697 |

*Primary Examiner*—William E. Kamm
*Attorney, Agent, or Firm*—Andrus, Sceales, Starke & Sawall

[57] ABSTRACT

A digital telemetry transmitter for transmitting eight channels of diagnostic quality electrocardiographic data has input circuitry for receiving analog EKG signals originating at electrodes on the patient. The input circuitry includes a circuit for ascertaining the impedance of the electrode connection to the patient and to indicate an electrode fault. EKG signals from the input circuit are provided to a digital/ analog converter for converting the analog signals into corresponding digital signals. The analog/digital converter may comprise an eight channel, 20-bit converter, sampling the input signals at a frequency of 10 KHz and providing a digital output signal having a frequency of 500 Hz. The output of the analog/digital converter is provided to a microprocessor control which provides a digital EKG modulating output signal. The output signal is periodically inverted to avoid stationarity in the transmitted data. The output signal includes error correction data that enables a receiver for the transmitted data to correct the digital EKG signal for noise. The microprocessor control changes the resolution of the transmitter when large signal changes occur in the data to accommodate such signals and to provide data compression. An rf signal generator generates an rf carrier signal. The modulating output signal of the microprocessor control is provided as a frequency modulating signal to the rf signal generator. The rf signal generator is stabilized against alterations due to reflected antenna loading.

46 Claims, 13 Drawing Sheets

Microfiche Appendix Included
(1 Microfiche, 26 Pages)

MULTIPLE CHANNEL BIOMEDICAL DIGITAL TELEMETRY TRANSMITTER

BACKGROUND OF THE INVENTION

The microfiche appendix comprising 1 microfiche and a total of 26 frames forms a portion of the present application.

The present invention relates to a multiple channel, biomedical, digital telemetry transmitter. Such a transmitter may be employed to transmit electrocardiographic (ECG or EKG) data from a patient to an electrocardiograph having a receiver so that the data may be analyzed to diagnose or evaluate the physiological condition or functioning of the patient's heart.

To obtain electrocardiographic data, a plurality of electrodes are placed at various locations on the chest and extremities of the patient in accordance with a medically accepted protocol. A patient cable has one end connected to the electrodes. In conventional electrocardiography, the other end of the patient cable is connected to the electrocardiograph. Conductors in the patient cable supply signals from the electrodes to the electrocardiograph. The electrocardiographic data, so supplied, may be displayed on a moving paper strip or a cathode ray tube of the electrocardiograph and/or may be stored in analog or digital form on an appropriate medium for analysis.

In electrocardiography employing telemetry, the other end of the patient cable is connected to a radio transmitter and the electrocardiograph has a radio receiver. The electrocardiographic data is transmitted to the electrocardiograph over the wireless link between the transmitter and the receiver.

The use of telemetry in electrocardiography has certain advantages. In hospital or other, similar setting, it is often desired to provide electrocardiographic data from a plurality of patients to a central station so that a single medical person can monitor the cardiac condition of the plurality of patients in an effective and efficient manner. Without telemetry, this often requires extensive wiring of the hospital to connect patient rooms to the central station. The wiring typically requires shielding to reduce the amount of electrical noise created in the signal during transmission from the patient rooms to the central station. The foregoing factors make such wiring costly. A wired system also has a certain amount of inherent inflexibility since there is always the possibility that electrocardiographic data must be obtained from a room or other location in the hospital that has not been wired.

The use of telemetry overcomes the foregoing problems.

Further, conventional electrocardiographic apparatus utilizing a patient cable between the patient and the electrocardiograph is generally limited to short term testing and/or to bedridden patients. In many circumstances, it is desired to obtain long term data and/or data from ambulatory patients.

To this end, portable electrocardiographic recorders have been developed, as typified by the well-known "Holter" recorder. These recorders contain a recording medium, such as a magnetic recording medium, that continuously records the electrocardiographic data of a patient over an extended period of time, such as 24 hours. The magnetic recording medium is inserted in a playback device for analysis and display purposes.

While such a recorder is capable of providing long term recording of electrocardiographic data from a patient, including an ambulatory patient, there is always a time delay between the acquisition of the electrocardiographic data and its review by medical personnel. Depending on the specific cardiac condition of the patient, this time delay may have serious medical consequences. The use of telemetry would overcome this time delay since the data could be sent directly and immediately to an electrocardiograph without the need for storage.

Still further, certain types of cardiac testing, such as stress testing, in which a patient runs on a treadmill, can be facilitated through the use of telemetry.

The foregoing circumstances have led to the increased use of, and interest in, telemetry in electrocardiography and other medical applications, such as electroencephalography. However, with existing telemetry equipment, it has heretofore been difficult, or impossible, to transmit biomedical data of the desired quality and quantity from the patient to the electrocardiograph.

To achieve a high degree of portability, the transmitter used in telemetry should be battery powered. The amount of power available to the telemetry transmitter is thus finite. Further, to facilitate patient comfort the batteries should be light in weight and small in size. At the same time however, the telemetry transmitter must operate for an extended period of time off the small batteries. For example, it is desirable for the telemetry transmitter to operate for 24 hours off the battery power supply. This allows the batteries to be changed once a day, ensuring they will be replaced in a routine, certain fashion and lessening the likelihood that the power supply will become exhausted and electrocardiographic or other biomedical data lost.

The foregoing considerations call for low power consumption by the telemetry transmitter from the battery power supply.

However, running contrary to the requirement for low power consumption is the desire to transmit increased quantities of electrocardiographic data of increased quality. This is particularly true where the electrocardiographic data is to be used for diagnostic purposes, as opposed to simple monitoring purposes. In monitoring, it is usually sufficient to provide a small amount of electrocardiographic data and only of a quality sufficient to allow large abnormalities in the data to be detected. Thus, at present, electrocardiographic telemetry systems of the type discussed above are generally capable of transmitting data capable of providing about three leads up to about seven leads of electrocardiographic data. This may not be adequate for diagnostic purposes.

In diagnostic electrocardiography, it is now deemed preferably, if not essential, to practice 12 lead electrocardiography in which eight EKG signals obtained from ten electrodes are simultaneously employed. The data must be of a quality that subtle alterations in any one, or all, of the leads is detectable.

As in all wireless communication systems, the electrocardiographic data in a biomedical telemetry system is transmitted from the transmitter to the receiver by altering, or modulating, a property, such as the frequency or amplitude, of a radio frequency carrier signal with a modulating signal representing the data.

Frequency modulation may be carried out at low power consumption but has not been heretofore capable of transmitting the desired quality and quantity of electrocardiographic data without employing a relatively wide bandwidth. This lessens the use that can be made of the available electromagnetic spectrum. Other modulation techniques, such as coherent phase shift keying, have been used to deal with these problems, but with a corresponding increase in power consumption from the finite power supply.

SUMMARY OF THE INVENTION

It is, therefore, the object of the present invention to provide a transmitter for a biomedical telemetry system which is capable of transmitting biomedical data of increased quantity and quality, while consuming small amounts of power from a finite power supply, such as a battery, and which employs a relatively narrow transmission bandwidth, thereby permitting efficient use of the electromagnetic spectrum.

More specifically, it is an object of the present invention to provide such a biomedical telemetry transmitter that can transmit eight channels of diagnostic quality electrocardiographic data for an extended period of time and employing a bandwidth of approximately 100 KHz.

These and other objects are achieved by employing frequency modulation to transmit the biomedical data in the telemetry transmitter of the present invention. Such modulation may be carried out at low power. The transmitted data is encoded to provide a high degree of informational efficiency thereto, thus enabling the telemetry transmitter of the present invention to transmit the desired quantity and quality of data in a narrow transmission bandwidth.

It is a further, more specific object of the present invention to provide such a telemetry transmitter in which the resolution of the transmitted data may be altered, thereby to provide compression to the transmitted data.

Another, more specific object of the present invention is to provide a biomedical telemetry transmitter providing improved error correction capabilities to the transmitted data.

Another object of the present invention is to provide a biomedical telemetry transmitter in which stationarity in the transmitted biomedical data may be avoided.

A further object of the present invention is to provide a biomedical telemetry transmitter that is stabilized in a highly efficient manner against frequency pulling resulting from changes in antenna loading reflected to the transmitter.

Yet another object of the present invention is to provide a transmitter for a biomedical telemetry system that enables the electrocardiographic electrodes, or other biomedical electrodes, to be tested for electrical qualities, for example impedance, to determine whether there is degradation or failure of one or more of the electrode connections to a patient.

A still further object of the present invention is to provide a biomedical telemetry transmitter having a display in which the electrical qualities of the electrode connection, and the existence and location of a failed electrode connection, are visually shown in a graphic manner.

Another object of the present invention is to provide a biomedical telemetry transmitter in which electrical phenomena caused by a cardiac pacemaker can be detected and an indication of the presence of same provided in the transmitted electrocardiographic data.

The manner in which these, and other, objects of the present invention are achieved will be apparent from the following detailed description thereof taken in conjunction with the accompanying drawing.

DETAILED DESCRIPTION OF THE PREFERRED EMBODIMENT

The Biomedical Telemetry System

Figure 1:
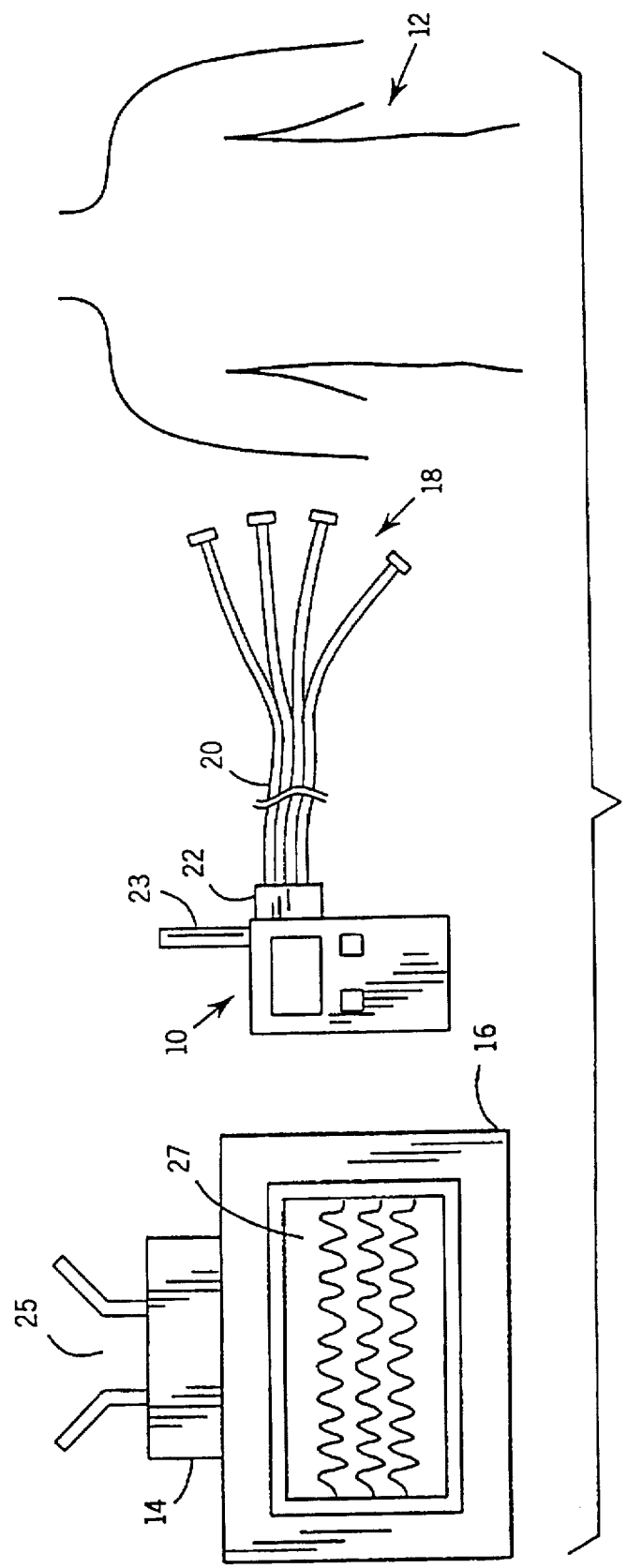
FIG. 1 is a view showing a biomedical digital multiple channel telemetry system incorporating the telemetry transmitter of the present invention.

In FIG. 1, a biomedical telemetry system includes telemetry transmitter 10 of the present invention for telemetering biomedical data, such as electrocardiographic data, from patient 12 to receiver 14 connected to electrocardiograph 16 for recording and analysis in the electrocardiograph.

To originate the electrocardiographic data, electrodes 18 are placed on the patient. For conventional 12 lead electrocardiography, ten electrodes 18 are positioned on the patient's skin at locations established by a recognized medical protocol. Four of the electrodes are placed on the patient to represent his/her limbs. These include the left arm (LA) electrode, the right arm (RA) electrode, the left leg (LL) electrode, and the right leg (RL) electrode. Six chest electrodes ($V_1$–$V_6$) are placed on the patient's chest at various locations near the heart.

Electrodes 18, applied to the skin of the patient, are each connected to one end of an electrical conductor. For ease of use, the individual conductors are usually combined into a single patient cable 20. The other ends of the individual conductors contained in patient cable 20 are connected to a plug 22 that is received in a corresponding receptacle in transmitter 10, in the manner shown in FIG. 1. Telemetry transmitter 10 has antenna 23 for transmitting electrocardiographic data to antennae 25 of receiver 14.

Telemetry receiver 14 is connected to electrocardiographic 16 so that the output of the receiver is provided to the electrocardiograph. The electrocardiographic data received by receiver 14 is stored in appropriate storage means in electrocardiograph 16 for analysis of the data. The data may be displayed in graphic form on moving paper strip 27.

The Telemetry Transmitter

Figure 2:
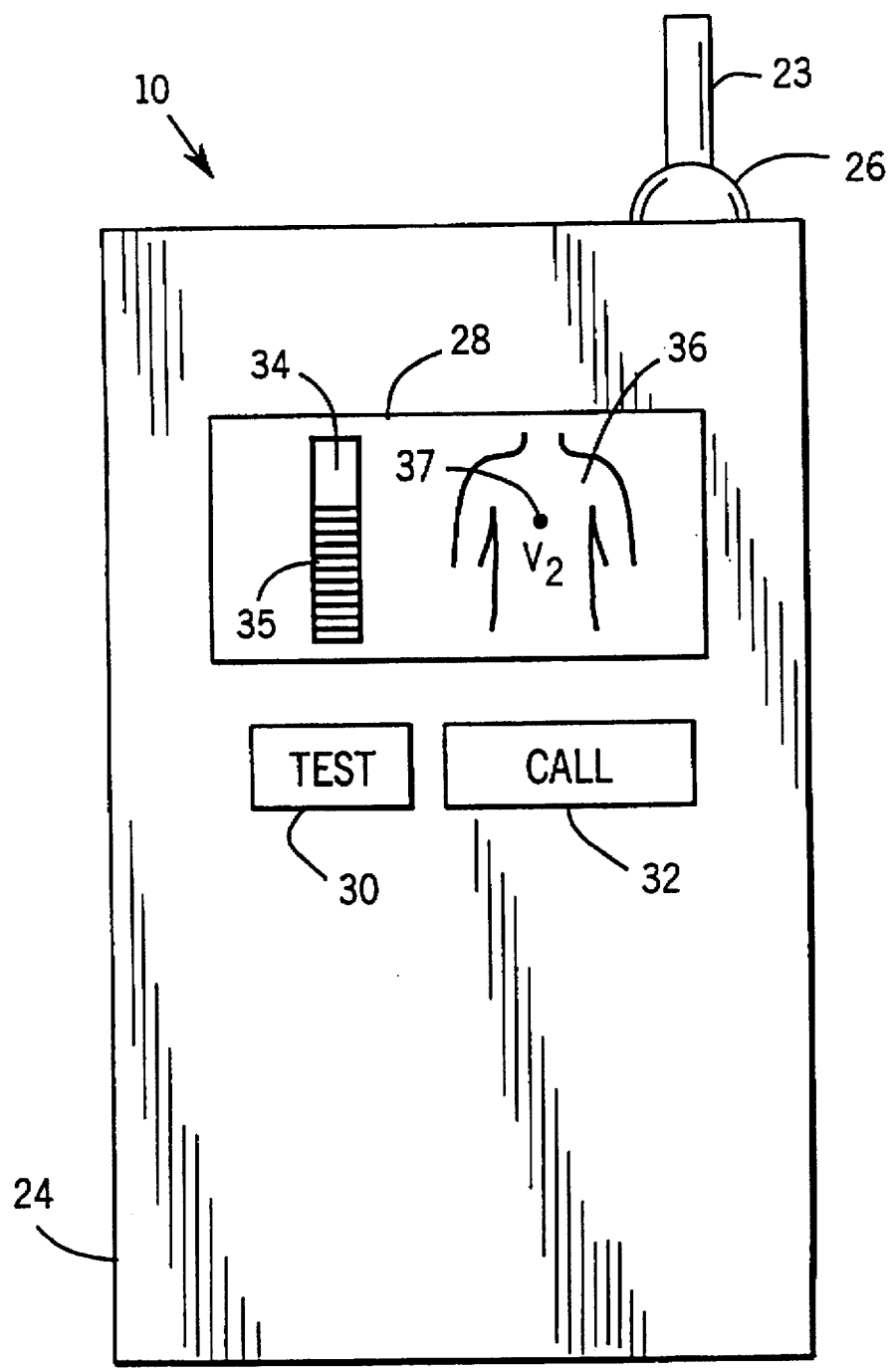
FIG. 2 is a view showing one side of the transmitter.

As shown in FIG. 2, telemetry transmitter 10 includes housing 24. Antenna 23 is mounted to housing 24 by collar 26. The front face of housing 24 contains a display module 28 that may, for example, be of the liquid crystal display (LCD) type. The front surface also includes a test button 30 and a call button 32. By pressing call button 32, the patient causes transmitter 10 to send a signal to receiver 14 to summon attending medical personnel. A speaker in housing 24 may provide audio feedback in the event call button 32 is pressed.

By pushing test button 30, it is possible to check the electrical quality of each of the electrocardiographic electrode connections to patient 12. As hereinafter noted in detail, this is accomplished by determining the impedance of each of the connections. High impedance is indicative of a poor electrical connection of an electrode to the patient and low electrical quality, and vice versa. Extremely high, or infinite, impedance indicates that an electrode has become disconnected from the patient and that an electrode fault has occurred.

To indicate the electrical quality of each electrode connection, a bar graph 34 showing lead quality is provided in display module 28. After pushing test button 30, call button 32 is sequentially pressed to check the quality of each of the electrodes, call transmission to receiver 14 being disabled during an electrode test sequence. The height of the graph 35 for each of the electrodes is an indication of the electrical quality of the connection, i.e. the higher the graph, the lower the impedance of the connection and the greater its quality.

As shown in FIG. 2, a torso image 36 is provided in display module 28. Torso image 36 contains indications, such as the dot shown as 37 and labelled "$V_2$", in FIG. 1 that indicates the location of the electrodes on the body of the patient. A fault at one of electrodes 18, for example, a disconnected electrode, causes the dot, such as dot 37, located on torso 36 at the position corresponding to that at which the faulty electrode is positioned on the body of patient body to blink on and off. A signal is also sent to receiver 14 that an electrode fault has occurred. This enables medical personnel attending the patient to determine quickly and accurately if, and where, a problem with the electrodes has occurred. During an electrode check, when the impedance of each of the electrodes is being checked, the dot and label corresponding to the electrode being checked will also be visible in display module 28.

Display module 28 may also provide an indication that the transmitter is "on" and that the power available from the batteries is low.

Figure 3:
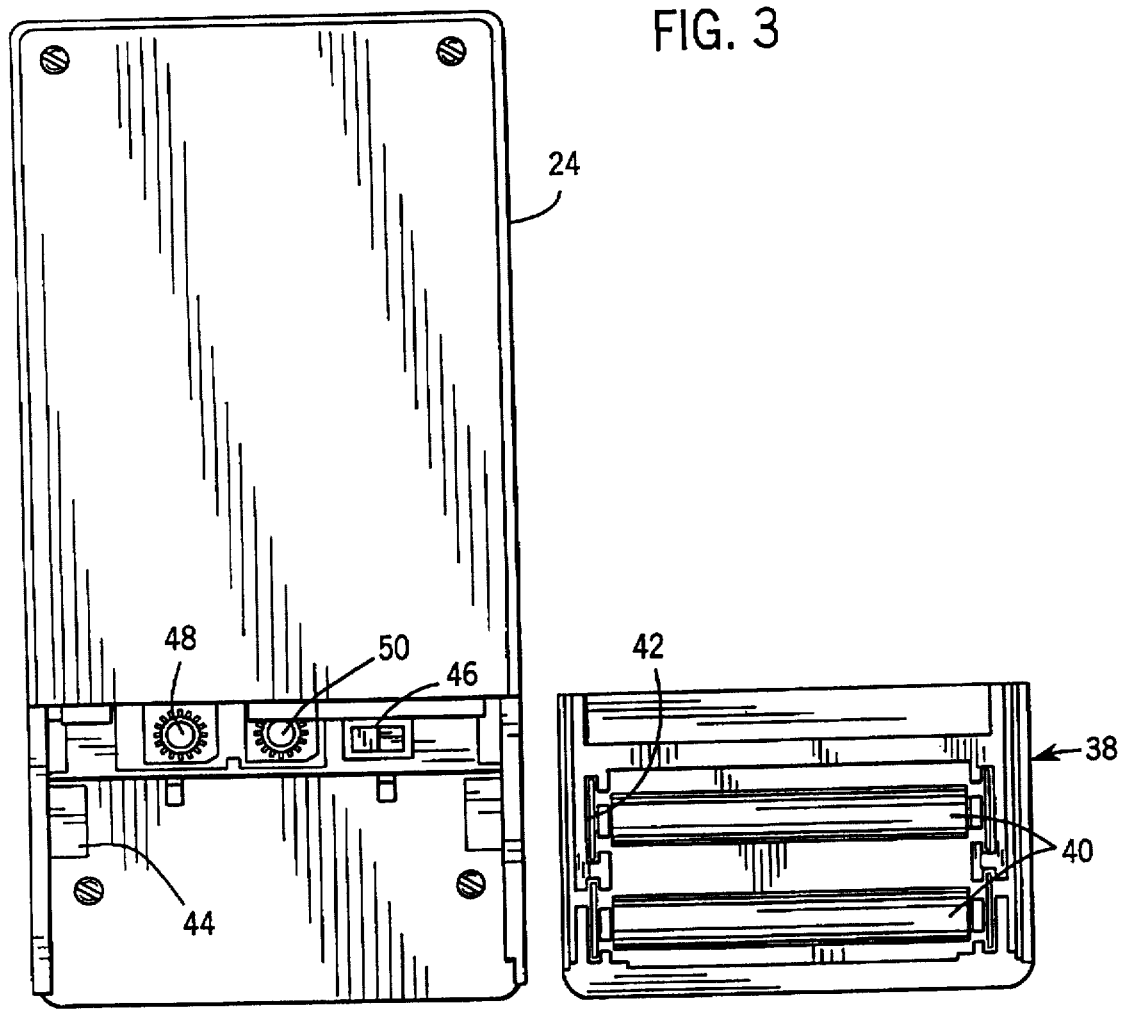
FIG. 3 is a view showing the other side of the transmitter with a panel of the transmitter removed.

The back surface of transmitter housing 24 includes a removable panel 38, as shown in FIG. 3. Panel 38 may be removed to insert batteries 40 that power transmitter 10 by sliding the panel off housing 24. Batteries 40 may be of the size designated by industry standards as AA and may be mounted on the inside of panel 38 and connected to the circuitry of transmitter 10 by spring loaded contacts 42 and 44.

The removal of panel 38 exposes on/off switch 46 for transmitter 10. It also exposes two frequency set switches 48 and 50. Switches 48 and 50 are used to set the frequency of the rf carrier signal used by transmitter 10 to transmit electrocardiographic data to receiver 14. For this purpose, switches 48 and 50 may comprise hexadecimal coded, rotary switches that may be rotated with the appropriate tool. The settings of switches 48 and 50 selects one frequency out of 256 discrete transmitting frequencies for transmitter 10 in the 902–928 MHz frequency band so that transmitter 10 transmits at the selected frequency between 904.76 and 925.24 MHz. The frequency may be selected in 80 KHz steps.

Figure 4:
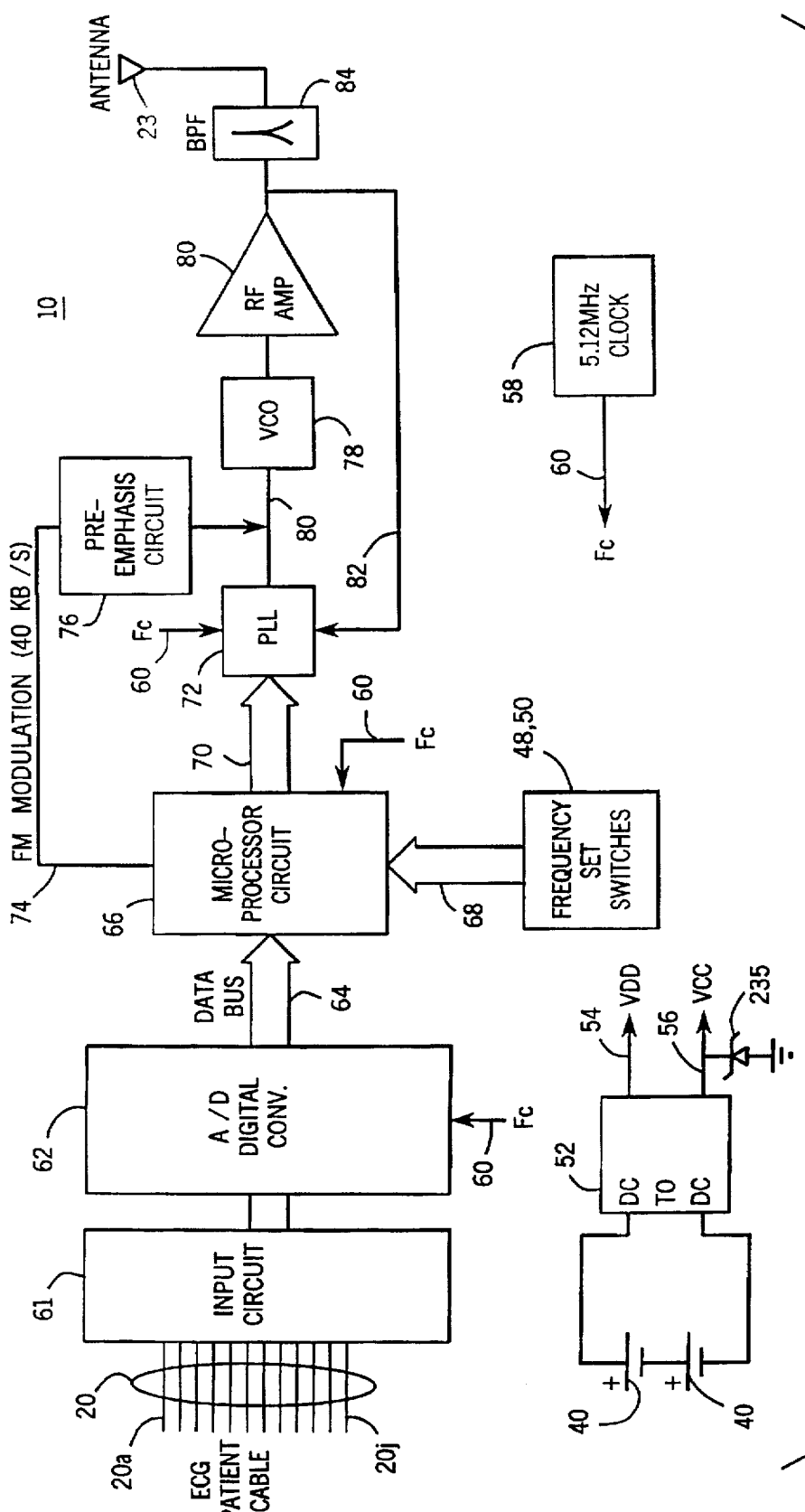
FIG. 4 is a general schematic diagram of the electrical circuitry of the transmitter.

FIG. 4 is a general schematic diagram of the circuitry of telemetry transmitter 10. As noted above, the circuitry of transmitter 10 is powered by a pair of batteries 40, connected in series and connected to dc-to-dc converter 52 that provides output voltages in conductors 54 and 56 of the magnitudes necessary for operating the circuitry of transmitter 10. For this purpose, dc-to-dc converter 52 may use switching regulators, such as those made and sold by Microlinear Corp. of San Jose, Calif. under the designation ML 4861.

Clock 58, which may be crystal controlled, provides a clock signal in conductor 60, that is used to coordinate and sequence the operation of the circuitry of transmitter 10. The clock output signal in conductor 60 may be 5.12 MHz and is subjected to division in the circuitries of transmitter 10, as required.

Figure 5:
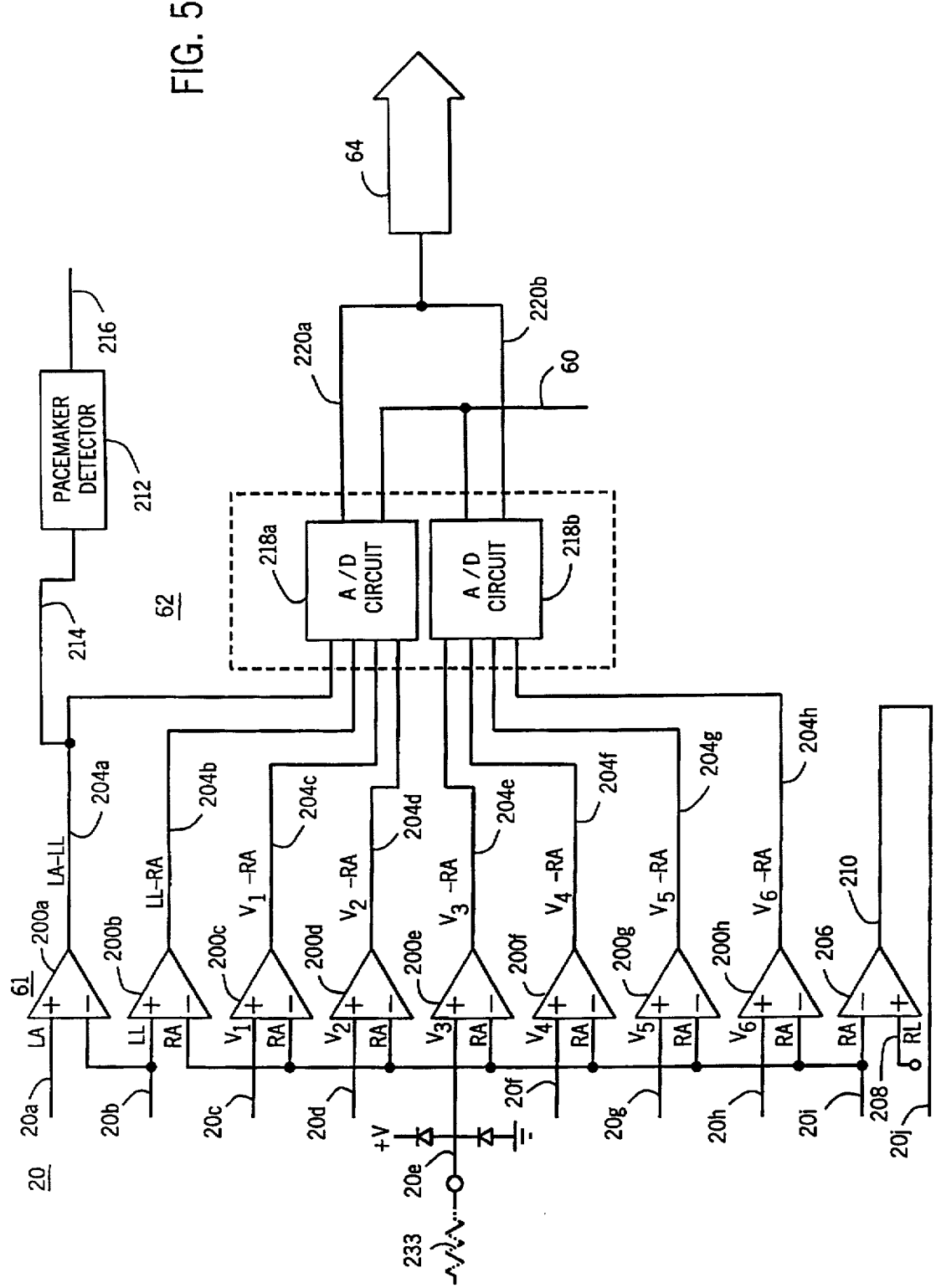
FIG. 5 is a schematic diagram of one embodiment of the input circuitry and analog/digital converter portions of the electrical circuitry shown in FIG. 4.

As shown in FIGS. 4 and 5, patient lead cable 20 containing conductors 20a–20j for electrodes 18 provides bipolarity analog voltage signals corresponding to the electrical potentials on the skin of the patient resulting from the activity of the heart. Conductors 20a–20j are connected through input circuitry 61 to the analog input of analog/digital converter 62. Patient cable 20 typically provides ten electrode connections, from which eight electrocardiographic signals are generated in input circuit 61. Each of the eight electrocardiographic signals is transmitted by transmitter 10, received by receiver 14, and utilized in electrocardiograph 16. The telemetry system shown in FIG. 1, and hence telemetry transmitter 10 of the present invention, may thus be said to have eight "channels" of electrocardiographic data.

Analog/digital converter 62 converts the analog voltage signal in each of the electrocardiographic channels to a corresponding digital signal. In a digital signal, the information content, in this case signal voltage magnitude, is expressed in a plurality of increments in which the digital signal is either of one signal state or another signal state. The increments are commonly known as "bits." The fact that the digital signal increments can be of only one state or another state, i.e. only two states, renders them "binary" in nature. One of the signal states is often termed "1" and the other signal state is often termed "0." The collection of bits used to express analog signal magnitude is termed a digital or binary "word", the most common digital word comprising eight bits and being termed a "byte." However, digital words may comprise any number of bits.

Analog/digital converter 62 carries out its conversion by periodically sampling or determining the magnitude of the analog signal and producing a corresponding digital signal. The sampling is carried out at predetermined intervals, known as the "sampling rate." For electrocardiography, a sampling rate of at least 500 Hz is commonly used. The output of clock 58 is provided to analog/digital converter 62 in conductor 60 for use in establishing the sampling frequency of analog/digital converter 62.

The output of analog/digital converter 62 is provided along digital data bus 64 to microprocessor circuit 66. The output of analog/digital converter 62 comprises a digital signal for each of the eight electrocardiographic signal channels in transmitter 10.

Microprocessor circuit 66 converts electrocardiographic digital input signals to a serial digital output signal in conductor 74 that may be used to frequency modulate the rf carrier signal of telemetry transmitter 10 with the electrocardiographic data. The serial data signal comprises a sequential series of bits. The rate at which the bits may occur in conductor 74 is 40 kilobits per second (40 KB/s). Microprocessor circuit 66 also adds error correction properties to the digital data signal that enables telemetry receiver 14 to correct for bit errors in the received signal. Microprocessor circuit 66 also establishes the resolution for the transmitted data.

Depending on the particular circuitry employed for input circuit 61, analog/digital converter 62, and microprocessor circuit 66, these portions of telemetry transmitter 10 may consume between 60 and 95 milliwatts of power.

The serial digital output signal from microprocessor circuit 66 is provided in conductor 74 through preemphasis circuit 76.

Microprocessor 66 determines the transmitting frequency of transmitter 10. For this purpose, the outputs of frequency setting switches 48 and 50 are provided as an input to microprocessor 66 in bus 68. Microprocessor 66 provides a control signal in bus 70, as determined by switches 48, 50, to the input of phase locked loop circuit 72 in the rf section of transmitter 10 that determines the operating frequency of the phase locked loop and hence the carrier frequency of the rf signal of transmitter 10.

The output signal produced by phase locked loop circuit 72 is provided to voltage controlled oscillator 78 in conductor 80 to control the output frequency of the oscillator, and hence the frequency of the rf carrier signal of transmitter 10. The modulating signal in conductor 74 is summed with the signal in conductor 80 from phase locked loop circuit 72 and is thus also provided to oscillator 78.

The alteration of the output signal from phase locked loop circuit 72 in conductor 80 by the modulating signal in conductor 74 deviates the frequency of the carrier signal produced by voltage controlled oscillator 78. For example, a data bit of one state may cause the oscillator to increase the frequency of the carrier signal. A data bit of the other state may cause the oscillator to decrease the frequency of the carrier signal. The electrocardiographic data is thus impressed on the carrier signal of telemetry transmitter 10. In a typical embodiment of the present invention, the modulating digital output signal may increase or decrease the frequency of the carrier signal by 35 KHz.

The rf section of transmitter 10 also includes radio frequency amplifier 80 coupled to the output of voltage controlled oscillator 78. The output of radio frequency amplifier 80 is provided as a feedback signal in conductor 82 to phase locked loop circuit 72. The output of radio frequency amplifier 80 is also provided through band pass filter 84 to antenna 23. The band pass filter 84, which may be of the ceramic, dielectric type, may have a band pass frequency of 915 MHz±12 MHz and is used to suppress harmonic radiation and other spurious signals so that telemetry transmitter 10 complies with the electromagnetic radiation requirements of various regulatory authorities. The signal at antenna 23 is provided to telemetry receiver 14.

The signal of clock 58 in conductor 10 is provided to microprocessor circuit 66 and phase locked loop circuit 72 for use in the operation of these circuitries.

Input Circuitry and Analog/Digital Converter

Figure 9:
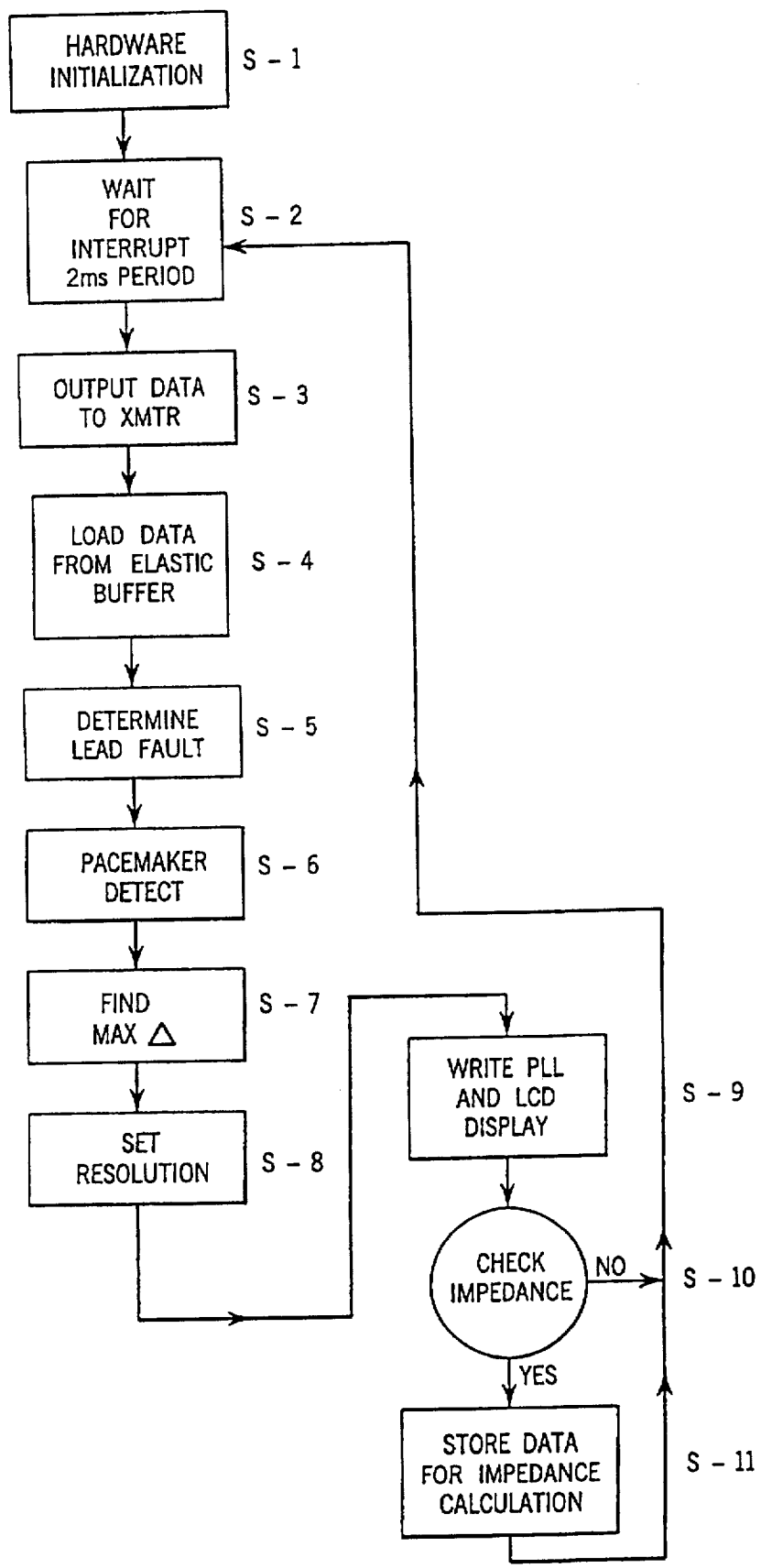
FIG. 9 is a flow chart illustrating the operation of a microprocessor found in the control portions of the telemetry transmitter.

FIG. 5 shows further details of input circuitry 61 and one embodiment of analog/digital converter 62. FIG. 9 shows another embodiment of analog/digital converter 62. The electrocardiographic signals from electrodes 18 are provided in patient lead cable 20 in conductors 20a–20j. These conductors are further identified in FIG. 5 by the location at which the electrode connected to the conductor is positioned. In these indicia, LA indicates the left arm electrode, LL indicates the left leg electrode, etc. Conductors 20a–20j of patient cable 20 are connected to input amplifiers 200a through 200h and 206 of input circuitry 61.

Input circuitry 61 contains circuitry for ensuring that if an electrode fault occurs, as by an electrode becoming disconnected from the patient, all electrocardiographic data being transmitted by transmitter 10 is not lost. The manner in which this is achieved is described, in detail, below. Input circuitry 61 also contains the circuitry shown in FIG. 6a that is used to determine the impedance of the electrocardiographic electrode connections when test button 30 and call button 32 of transmitter 10 are operated. Input circuit 61 also includes circuitry to protect transmitter 10 against excessive voltages applied to transmitter 10 when a patient having electrodes 18a–18j applied to his/her chest undergoes defibrillation, also as described, in detail, below.

Amplifiers 200 and 206 comprise differential amplifiers having the electrodes located at various positions on the body connected in pairs to their inputs. The outputs of differential amplifiers 200 comprise the electrocardiographic signals for the signal or data channels of telemetry transmitter 10. Thus, as shown in FIG. 5, the inputs to differential amplifier 200a comprise the signal in conductor 20a from the electrode providing the left arm (LA) signal and the signal in conductor 20b providing the left leg (LL) electrocardiographic signal; the inputs to differential amplifier 200b comprise the signal in conductor 20b providing the left leg (LL) electrocardiographic signal and the signal in conductor 20i comprising the right arm (RA) electrocardiographic signal.

The outputs of amplifiers 200 are provided in conductors 204a–204h. The signal in conductor 204a containing the output of differential amplifier 200a comprises the difference between the signal in conductor 20a connected to the left arm (LA) electrode and the signal in conductor 20b connected to the left leg (LL) electrode. The lead signal in conductor 204a may thus be termed the LA-LL signal. Differential amplifiers 200b–200h are connected in an analogous manner and the designation of the signals provided at the outputs of amplifiers 200b–200h supplied in conductors 204b–204h shown in FIG. 5. Each of differential amplifiers 200b–200h has one input connected to conductor 20i containing the electrocardiographic signal from the right arm (RA).

Conductor 20i containing the electrocardiographic data produced by the electrode positioned to provide the right arm (RA) data is also provided to high gain amplifier 206. The other input to amplifier 206 is connected to the circuit reference by conductor 208. The output of amplifier 206 in conductor 210 is provided to conductor 20j connected to the electrode located at a position representing the right leg (RL). Conductor 20j becomes a lead driven by the output of amplifier 206 in conductor 210. Amplifier 206 attempts to drive the patient's body to the circuit reference. This provides improved common mode rejection inasmuch as the patient's body and the circuitry, in effect, share a common reference.

It is important to ensure that if one electrode becomes disconnected from the patient, the remaining data being transmitted by transmitter 10 does not become so distorted as to be unintelligible. This permits some utility to be preserved in the remaining electrocardiographic data until the connection of the missing electrode can be restored.

To this end, as will be noted from FIG. 5, the input signals to differential amplifier 200a comprise the left arm (LA)

signal in conductor 20a and the signal in conductor 20b comprising the electrocardiographic data representing the left leg (LL). All the remaining amplifiers 200b–200h have one of their inputs connected to the signal in conductor 20i containing the electrocardiographic data representing the signal from the patient's right arm (RA). The other inputs of each of amplifiers 200b–200h contain signals from one of the remaining electrodes connected to the patient.

With the input configuration shown in FIG. 5, if any one electrode becomes disconnected, there will be at least one channel, the integrity of which is maintained, notwithstanding the disconnection. Very likely there will be additional channels in which the integrity is maintained. Even if the electrode providing the right arm (RA) signal is lost, the operation of differential amplifier 200a connected to the conductor providing the left arm (LA) signal and the conductor providing the left leg (LL) is not affected. This channel would continue to provide electrocardiographic information so that all signal data does not become lost.

Figure 6A:
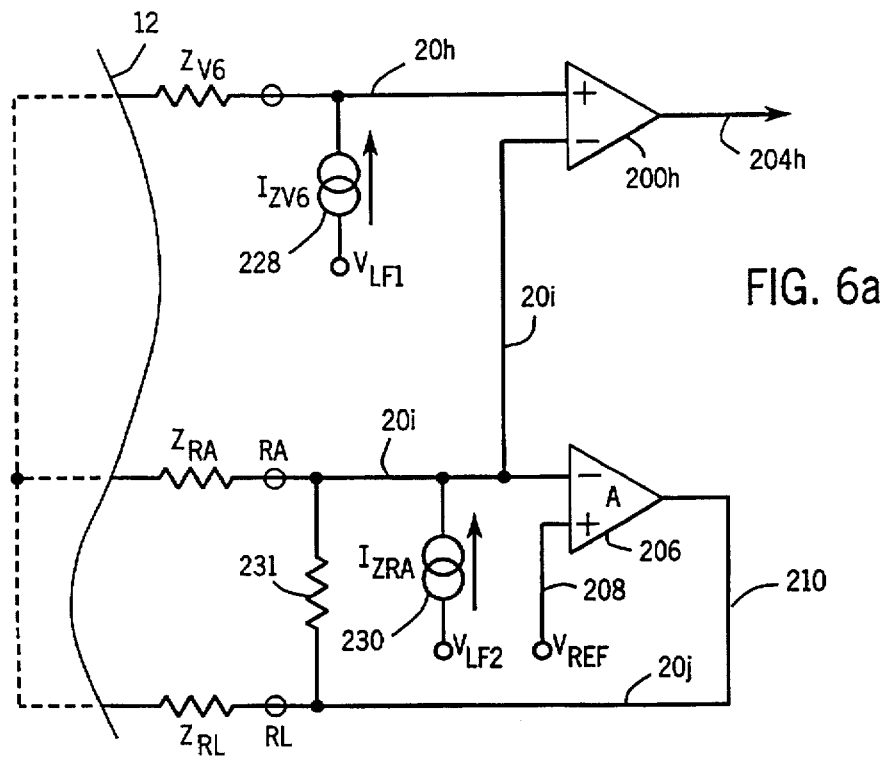
FIGS. 6a and 6b show circuitry, and the operation thereof, employed to measure the impedance of the connection of the electrocardiographic electrodes to a patient.
Figure 6B:
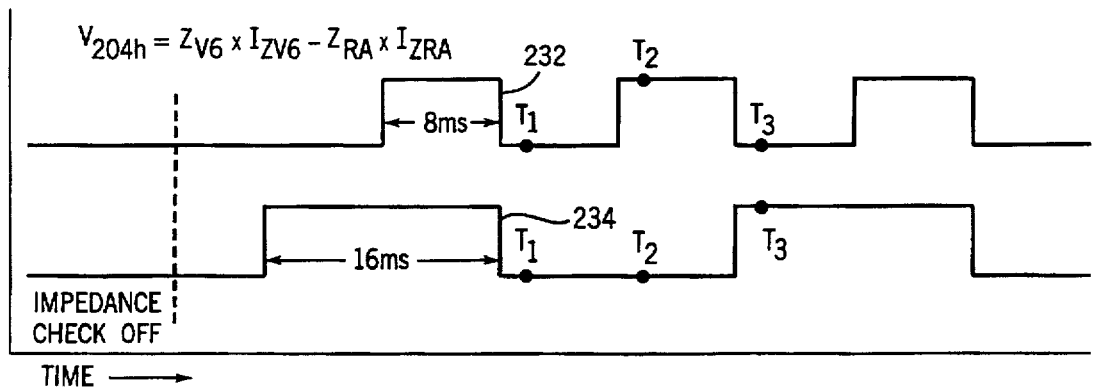

FIGS. 6a and 6b show the manner in which the impedance of the connection of electrodes 18 to patient 12 is ascertained to determine loss of an electrode connection or a high impedance connection. Elements shown in FIG. 6a corresponding to those in FIG. 5 have been identified with similar reference numbers.

An impedance check may be performed after the electrodes have been applied to the patient and before the transmission of electrocardiographic data. By checking the impedance in each electrode, medical personnel can determine whether additional preparatory measures are needed to reduce the impedance in an electrode so that data of the desired quality can be transmitted for the desired period of time. For example, if the skin of the patient is dry, as is often the case in older patients, this may result in high impedance in the electrode connection. If this is the case, it will be necessary for the technician to scrape or otherwise treat the skin, as by moisturizing, to reduce the impedance in the connection of the electrode.

For exemplary purposes FIG. 6 shows the circuitry used to ascertain the impedance of the elements used to provide the $V_6$ and RA electrocardiographic signals.

The impedance quantities $Z_{V6}$, $Z_{RA}$, and $Z_{RL}$ shown in FIG. 6a represent the impedance seen by the electrodes 18 applied to the body of the patient 12 to provide the $V_6$, RA, and RL electrocardiographic signals, respectively.

A current source 228, which may be a large resistor driven by a voltage source $V_{LF1}$, is connected to conductor 20h at the non-inverting input of differential amplifier 200h. The resistance of the resistor of current source 228 is large compared to normal electrode impedance. Conductor 20h contains the signal from the electrode providing the electrocardiographic signal corresponding to the $V_6$ electrode location. The other input to differential amplifier 200h is the signal in conductor 20i connected to the electrode providing electrocardiographic data representing the right arm (RA) of the patient.

A large resistor, current source 230 is also connected to conductor 20i at the inverting input of amplifier 206. The resistor of current source 230 is driven by voltage source $V_{LF2}$. The other input to amplifier 206 is a reference voltage $V_{REF}$. The output of amplifier 206 is connected to the right leg (RL) electrode used to provide the improved common mode rejection noted above. Resistor 231 is connected across conductor 20i and conductor 20j.

The following technique is used to determine whether a connection of one of the electrodes to the patient has been lost.

Should the $V_6$ electrode become disconnected from patient 12, the signal in conductor 20h will assume the magnitude of the positive voltage $V_{LF1}$ since there is now no current flow through current source 228. This will cause a high voltage of one polarity to appear at the output of differential amplifier 200h. This high voltage signal is applied to microprocessor circuit 66 and used to indicate to receiver 14 and display module 28 that loss or failure of the $V_6$ electrode connection has occurred.

Should the connection for the right arm (RA) electrode be lost, the following will occur. Amplifier 206 is a high gain amplifier that drives the signals at the non-inverting and inverting inputs to the same level. If the right arm (RA) electrode becomes disconnected, the voltage in conductor 20j becomes negative in order to draw current out of current source 230 through resistor 231. The negative voltage in conductor 20j appears in the body of patient 12 and in conductor 20h. This drives amplifier 200h to produce a high voltage of the opposite polarity to that produced with the loss of the $V_6$ electrode. This high voltage of the opposite polarity is used by microprocessor circuit 66 as a detection for the loss or failure of the right arm (RA) electrode. Microprocessor circuit 66 may continuously monitor the outputs of differential amplifiers 200 for the high voltages indicative of electrode connection failure.

The following technique is used when it is desired to measure the impedance of the electrode connections to the patient, using the $V_6$ and right arm (RA) electrodes as examples. Because amplifier 200h is a differential amplifier, the output voltage in conductor 204h will be equal to the voltage at the non-inverting input less the voltage at the inverting input. Disregarding for the moment the effect of the electrocardiograph signal in the electrodes, the output voltage of differential amplifier 200h connected to the $V_6$ and right arm (RA) electrodes is proportional to a voltage comprising the impedance $Z_{V6}$ of the $V_6$ electrode connection times the current $I_{ZV6}$ provided by current source 228 minus a voltage comprising the impedance $Z_{RA}$ of the right arm (RA) electrode connection times the current $I_{ZRA}$ provided by current source 230, or $$V = Z_{V6} \times I_{ZV6} - Z_{RA} \times I_{ZRA}$$

In order to obtain the quantities necessary to solve the foregoing equation, the energization of current sources 228 and 230 by the voltage sources to which they are connected is altered to provide the current pulses shown in FIG. 6b. For this purpose, the energization of the current sources by the voltage sources may be controlled by microprocessor circuit 66. Current source 228 provides a series of 8 ms current pulses 232 shown in FIG. 6b as a result of increasing the voltage $V_{LF1}$ applied to it. Current source 230 provides a series of 16 ms current pulses 234 as a result of increasing voltage $V_{LF2}$ applied to it. The current pulses are sequenced in the manner shown in FIG. 6b.

Prior to the time shown by the vertical dotted line in FIG. 6b, no impedance check is being carried out and the energization of the voltage sources for current sources 228 and 230 is not altered. Following the time shown by the vertical dotted line, an impedance check of the $V_6$ electrode and the right arm (RA) electrode is commenced by the operation of buttons 30 and 32 and the generation of the current pulses shown in FIG. 6b.

Time $T_1$ in FIG. 6b shows a condition in which no current pulses are being generated. The voltages $V_{LF1}$ and $V_{LF2}$ applied to the resistors forming the current sources are the normal voltage of the voltage supplies.

At time $T_2$ the voltage $V_{LF1}$ applied to the resistor of current source 228 is increased. This will increase the current $I_{ZV6}$ by a known amount. This increase in current when applied to impedance $Z_{V6}$ will generate an increased voltage to the input of amplifier 200h. The other input signal to amplifier 200h in conductor 20i will not change since there is not change of the energization $V_{LF2}$ to current source 230. Since the amount of current change applied to impedance $Z_{V6}$ is known, the change in the output voltage of differential amplifier 200h in conductor 204h will be a function of the impedance $Z_{V6}$ of the $V_6$ electrode. The output of amplifier 200h can be measured by microprocessor circuit 66 to determine the impedance of the $V_6$ electrode connection.

The impedance of the right arm electrode may be determined in a similar manner at a time $T_3$ where the energization $V_{LF2}$ of current source 230 is increased but not the energization $V_{LF1}$ of current source 228 so that the change in the output of amplifier 200h is a function of the impedance $V_{RA}$ of the right arm (RA) electrode connection.

The changes in the output of amplifier 200h at times $T_2$ and $T_3$ are obtained for a plurality of such times and averaged to reduce or eliminate the effects of the electrocardiographic signals from the patient in electrodes 18 which also appear in conductors 20h and 20i.

It will be appreciated that the circuitry shown in FIG. 6a will be provided in conjunction with each of amplifiers 200a–200h to determine electrode connection failure and the impedance of each electrode connection.

FIG. 5 also shows the circuitry employed to provide defibrillator protection to transmitter 10. Should the patient to whom electrodes 18 are applied require defibrillation to restore rhythmic beating of the heart muscle, high-voltage electrical heart stimulation is applied to the patient by a defibrillator. Unless precautions are taken, these high voltage signals may adversely affect the circuitry and operation of telemetry transmitter 10.

To provide protection against defibrillation signals, resistors, such as resistor 233 shown in conductor 20e, shown in FIG. 5 may be inserted in each of conductors 20a–20j of patient cable 20. Two diodes are connected to each of the conductors 20a–20j to provide a shunt path for the high voltages of defibrillation away from the remaining portions of transmitter 10. The diodes connected to each conductor are connected to a zener diode 235 connected to power supply 52, as shown in FIG. 4 to provide a return path for the defibrillation voltages.

Input circuitry 61 may also include pacemaker detection circuity to detect the rapidly changing voltages associated with a pacemaker spike and provide a signal to microprocessor circuit 66. Microprocessor circuit 66 provides data in the signal transmitted by transmitter 10 that inserts a flag or marker in the data stored in receiver 14 that can be used to analyze the operation of the pacemaker. A pacemaker detection circuit is typically connected to the output of each of amplifiers 200a through 200h and 206. One such circuit is shown in FIG. 5 as pacemaker detection circuit 212 connected to conductor 204a by conductor 214. The output of pacemaker detection circuit 212 is provided in conductor 216 to microprocessor circuit 66. Pacemaker detector 212 may comprise a high pass filter for the high frequency pacemaker spikes having a duration of one millisecond or less. The output of the high frequency filter is provided to a comparator that provides an enhanced square wave signal suitable for provision to microprocessor circuit 66.

The electrocardiographic channel signals in conductors 204a–204h from differential amplifiers 200a–200h are provided to the input of analog/digital converter 62. As shown in FIG. 5, the signals in conductors 204a and 204h may be provided in parallel to the input of analog/digital converter 62. Analog/digital converter 62 converts the analog voltage signals in conductors 204a–204h into corresponding digital signals for provision to data bus 64.

Analog/digital converter 62 may comprise a pair of analog/digital converter integrated circuits 218a and 218b, such as those made and sold by Analog Devices, Inc. of Norwood, Mass. under the designation AD771. Circuits 218a and 218b may comprise analog/digital converters of Sigma-Delta type. Each of analog/digital converter circuits 218 receives four channel inputs. For example, circuit 218a receives the channel inputs in conductors 204a–204d. Circuit 218b receives the channel inputs from conductor 204e–204h. Analog/digital converter circuits 218 also receive the clock signal in conductor 60 which is used to establish the sampling rate. The sampling rate of analog/digital circuits 218a and 218b may be 500 Hz.

The output of analog/digital circuits 218a and 218b are provided in buses 220a and 220b to data bus 64. The output from analog/digital circuits 218a and 218b is typically provided in a data format in which the signal magnitude is expressed in digital words of 8 or 16 bits, i.e. one or two bytes.

Analog/digital circuits 218a and 218b may consume approximately 80 milliwatts of power.

Figure 7:
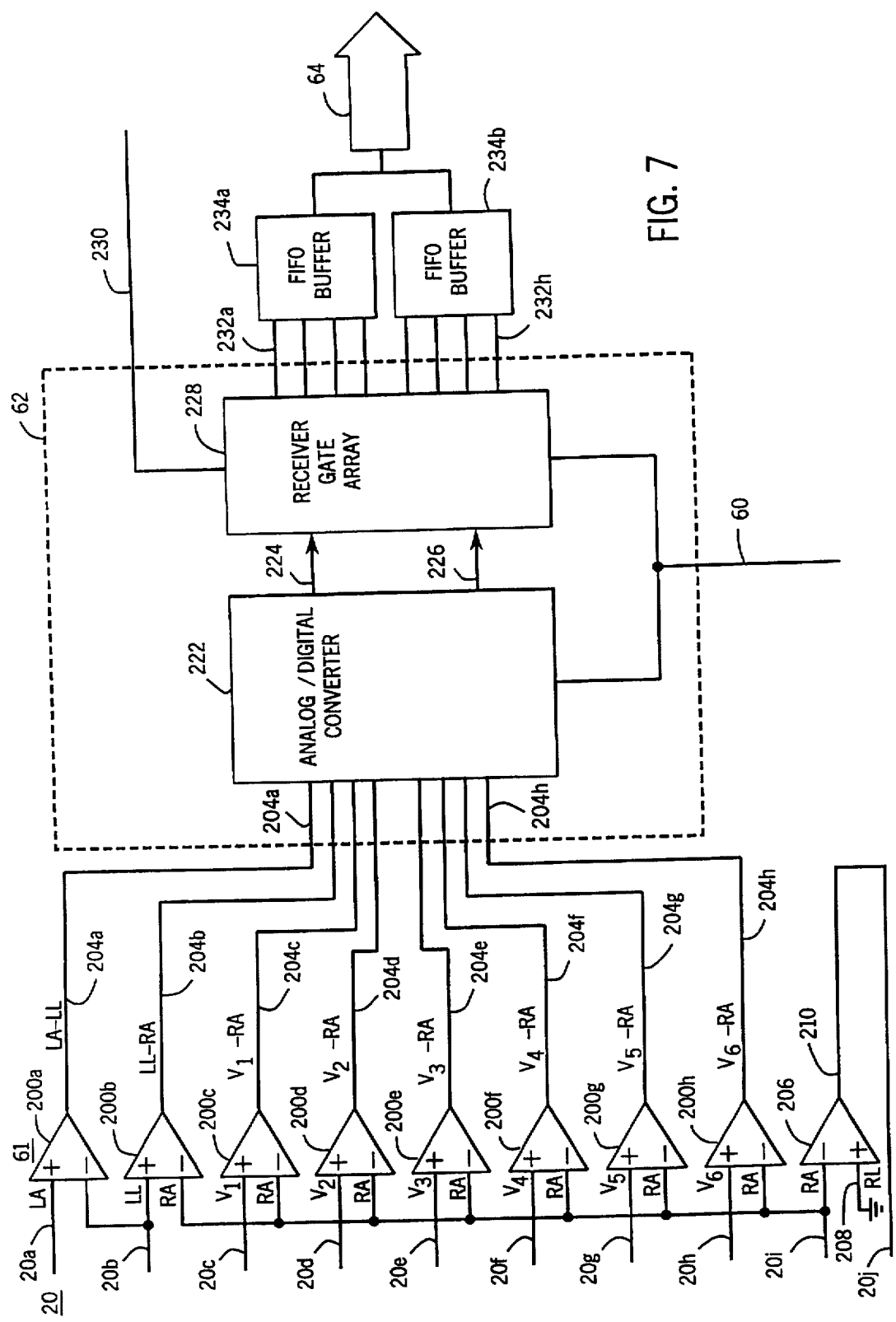
FIG. 7 is a schematic diagram showing another embodiment of the input circuitry and analog/digital converter portions.

Another embodiment of analog/digital circuit 62 is shown in FIG. 7. In the analog/digital converter shown in FIG. 7, the electrocardiographic channel signals in conductors 204a–204h are provided to the input of an 8-channel, 20-bit analog/digital converter 222 operating at a sampling frequency of 10 KHz. This sampling rate is substantially higher than the 500 Hz sampling rate that typifies the analog/digital converter shown in FIG. 5. Analog/digital converter 222 may comprise that integrated circuit element made and sold by Mortara Instrument, Inc. of Milwaukee, Wis., under the part designation 299-0014. Analog/digital converter 222 resembles an analog/digital converter of the multi-bit Sigma-Delta type.

Analog/digital converter 222, by virtue of employing a 10 KHz sampling rate and 20 bits to convert the analog signal provides highly accurate analog/digital conversion having a one microvolt resolution over a one volt range. In addition to providing highly accurate analog/digital conversion, analog/digital converter 222 may operate at low power. This is by virtue of being optimized to signal characteristics encountered in biomedical applications. Analog/digital converter consumes approximately 45 milliwatts of power.

Analog/digital converter 222 also receives the clock signal in conductor 60.

Figure 8:
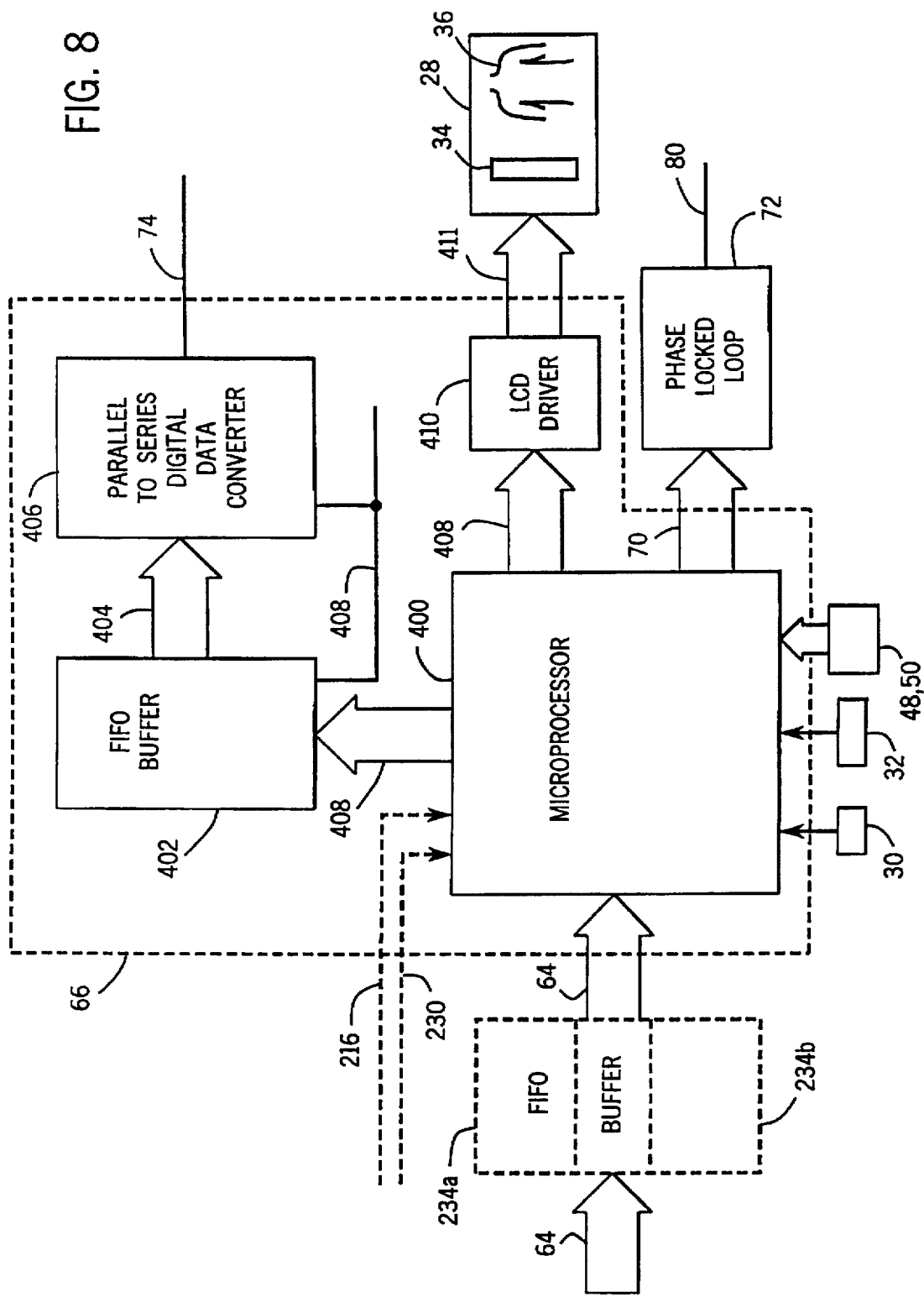
FIG. 8 is a schematic diagram showing the control portions of the electrical circuitry shown in FIG. 4.

The high sampling rate employed by with analog/digital converter 222 also enables analog/digital converter 62 shown in FIG. 8 to obtain high frequency characteristics of the electrocardiographic data, such as pacemaker spikes. Analog/digital converter 222 contains an internal slew rate detector which may be used to detect pacemaker spikes. A slew rate detector detects the amount of change or "slew" occurring in two successive samples of the electrocardiographic data. With digital words of a given length, there is a limit to amount or rate of change that can be reflected in two successive digital words. A slew rate detector determines when this maximum amount of change is equalled or exceeded so that the circumstance is reflected in the operation of the analog/digital converter. Since a pacemaker spike is characterized by very rapid changes in signal magnitude, it drives the slew rate detector to the limit condition. This is used as an indication that a pacemaker spike has occurred. The digital output of analog/digital converter 222 would contain a corresponding indication of the occurrence. The use of the high sampling frequency and internal slew rate detector for pacemaker spike detection, avoids the need for separate circuitry, such as that shown in FIG. 5.

Analog/digital converter 222 may consume 45 milliwatts of power.

The output of analog/digital converter 222 is provided in conductor 224. The output of analog/digital converter 222 is a serial, digital signal in which each of the eight channels of electrocardiographic data provided by conductors 204a–204h appear in seriatim as a high speed serial digital stream. The signal may have a frequency of 2.56 MHz. Every 100 microseconds in the signal, a 20-bit word for each of the eight electrocardiographic channels, as well as other ancillary information necessary for controlling and synchronizing the operation of the circuitry is provided in conductor 224. The use of a serial data stream facilitates the provision of the electrical isolation should same be required in the biomedical device, since only a single isolating device, such as a pulse transformer or an optical isolator, need be employed in conductor 224. Analog/digital converter 222 may also provide an electrically isolated clock output signal in conductor 226.

The serial data signal in conductor 224 and the clock signal in conductor 226 are provided to receiver gate array 228. Receiver gate array 224 may comprise the component manufactured and sold by Mortara Instrument, Inc. of Milwaukee, Wis. under the designation 2999-101B. The circuitry in receiver gate array 224 comprises a plurality of shift registers and adders that carry out a series to parallel conversion of the serial data stream from analog/digital converter 222 in conductor 224. Receiver gate array 228 also carries out a decimation by twenty function that reduces the 10 KHz sampling rate of analog/digital converter 222 to a 500 Hz operating rate for the remaining portions of telemetry transmitter 10. This decimation by twenty function may be carried out by averaging twenty consecutive digital signals for each channel into a single average value.

Every 2 ms, receiver gate array 228 sends out, in parallel data format, two 16-bit words for all eight electrocardiographic data channels in conductors 232a–232h. The data for each channel is, thus, a 32-bit word which includes the decimated EKG data, and one bit for pacemaker spike detection. The data for all eight channels is typically sent in 20 microsecond bursts in each 2 ms interval. During the 20 microsecond burst, a disable signal from receiver 228 is sent to microprocessor circuit 66 in conductor 230 to disable the microprocessor circuit. The short data transmission burst of 20 microseconds allows microprocessor circuit 66 to work during the remaining portions of the 2 ms intervals. This allows the microprocessor circuit to work in an efficient, low power manner.

The signal from receiver gate array 228 in conductors 232a–232h is provided to input elastic buffers 234a and 234b. Buffers 234a and 234b operate on a first in-first out basis to provide the data from analog/digital converter 62 to microprocessor circuit 66 in data bus 64.

Controller

As shown in FIG. 8, microprocessor circuit 66 includes microprocessor 400. Microprocessor 400 may be selected from the family of microprocessors made and sold by Motorola, Inc. of Schaumburg, Ill. under the general designation HC11 Microprocessors. The microprocessor made and sold by Motorola and having the designation MC68HC711D3CFN2 has been found suitable for use in microprocessor circuit 66 of telemetry transmitter 10. Microprocessor 400 may be programmed in accordance with the computer program listing contained in the Appendix. Microprocessor circuit 66 may consume approximately 15 milliwatts of power. This includes the power used by receiver gate array 228 in the embodiment of the invention shown in FIG. 7.

Microprocessor 400 receives the data signals in bus 64 from the analog/digital converter or from buffer 234 and provides a parallel formatted, electrocardiographic data output in bus 408 to buffer circuit 402 that is used to form the modulating electrocardiographic data output signal in conductor 74. Buffer circuit 402 operates on the first in-first out basis to coordinate the electrocardiographic data output of microprocessor 400 with the other portions of microprocessor circuit 66 that receive and utilize the output of microprocessor 406. The use of buffer 234 at the input to microprocessor 400 and the use of buffer 402 at the output of microprocessor 400 permits the short term storage of data signals, thereby allowing for flexibility and efficiency in the operation of microprocessor 400. Buffers 234 and 402 may comprise short term digital data storage registers.

The output of buffer circuit 402 is provided in data bus 404 to parallel to series converter 406. Parallel to series converter 406 converts the parallel data format provided by data bus 404 to a series data format output in conductor 74 for provision to the input of voltage controlled oscillator 78 as the electrocardiographic data modulating signal. Buffer circuit 402 and converter 406 receive a clock signal in conductor 408 derived from the output signal in conductor 60 from clock 58. The input to converter 406 operates at a frequency of 5 KHz. The parallel formatted data in bus 404 is in the form of 8-bit digital words so that the data rate in conductor 74 of the output of converter 406 becomes the 40 kilobits per second, noted above. Parallel to series data converter may be the element made and sold by Texas Instruments, Inc. of Dallas, Tex. under the designation 74HC151.

The manner in which the serial data signal stream appears in conductor 74 as a result of the operation of microprocessor 400 and parallel/series digital data converter 406 is shown below. The data is organized into data packets or frames, each of which may occupy a time interval of 8 ms. In each frame there are four electrocardiographic data samples. Each data sample contains eight digital signals on of which corresponds to the magnitude of the EKG signal in one of the eight EKG channels. The organization of the data frames is shown below, along with the number of bytes allocated to each component in a typical data frame.

| BYTES | SIMPLIFIED DATA STRUCTURE |
| --- | --- |
|  | INVERTED BARKER |
|  | PROGRAM NUMBER |
|  | HIGH SPEED STATUS |
|  | SAMPLE #1A |
|  | SAMPLE #2A INVERTED |
|  | SAMPLE #3A |
|  | SAMPLE #4A INVERTED |
| 2 | BARKER |
| 1 | CHANNEL NUMBER |
| 1 | HIGH SPEED STATUS |
| 9 | SAMPLE #1B |
| 9 | SAMPLE #2B INVERTED |
| 9 | SAMPLE #3B |
| 9 | SAMPLE #4B INVERTED |

| BYTES | SIMPLIFIED DATA STRUCTURE |
|---|---|
| | BARKER |
| | LEAD FAIL |
| | HIGH SPEED STATUS |
| | SAMPLE #1C |
| | SAMPLE #2C INVERTED |
| | SAMPLE #3C |
| | SAMPLE #4C INVERTED |
| | BARKER |
| | LOW SPEED STATUS |
| | HIGH SPEED STATUS |
| | SAMPLE #1D |
| | SAMPLE #2D INVERTED |
| | SAMPLE #3D |
| | SAMPLE #4D INVERTED |
| | REPEAT |

It will be seen that four data frames are serially provided to conductor 74 on a repetitious basis. The samples in the four data frames are identified by the letters A through D.

Each data frame comprises 40 bytes of data. As shown above in connection with the second data frame, the first two data bytes are so-called "Barker" data. Barker data, named after the developer thereof, is a mathematical or statistically determined series of bits that have a low probability of occurring in actual EKG data. This enables the Barker data to be used to identify the beginning of a data frame in the serial data stream in conductor 74 and, particularly so that the circuitry of receiver 14 can identify the beginning of a data frame in the serial data stream by identifying the unique pattern of the Barker data during data recovery in the receiver.

The next, or third, data byte is used for a plurality of purposes noted, in detail, below.

The next, or fourth, data byte is used to indicate the "high speed status" of the telemetry system. More particularly, it is used to indicate whether there has been a failure of the right arm (RA) electrode, the signal of which is supplied to each of differential amplifiers 200b–200h and amplifier 206 in input circuitry 61, as shown in FIG. 5. Failure of this lead will result in the loss of all EKG data, except the LA–LL electrode output of differential amplifier 200a.

The fourth data byte is also used to indicate the existence of pacemaker signals in the data samples being transmitted in the data frame. This is used by receiver 14 to insert a marker in the received data.

The remaining 36 bytes in the data frame contain the EKG data. The EKG data is broken down into four sample units 1–4, each of which contains one data sample for each of the eight EKG channels, plus the error correction data described below. Each of the sample units 1–4 comprise 9 bytes. Each byte has eight bits. There are eight 8-bit bytes of EKG data, one for each EKG channel, and one 8-bit error correction byte.

As noted above, the third byte in each data frame is used for a variety of purposes. In the first data frame, the third byte is used to identify, to telemetry receiver 14, the particular configuration of the microprocessor 400 in telemetry transmitter 10. In the second data frame, the third byte is used to identify the transmitting frequency or transmitting channel number, as determined by frequency set switches 48 and 50. The transmitting channel number is a binary number from 1 to 256 that serves to identify the transmitter, and hence the patient, from which the data is being sent. This data is used by telemetry receiver 14 to detect cross-talk from other transmitters that may be present as, for example, in a hospital setting. In the third data frame, the third data byte is used to signal to the receiver that an electrode connection failure has occurred at the patient at an electrode other than the right arm (RA) electrode. In the fourth data frame, the third data byte is used to indicate the "low speed status" of the telemetry system. The low speed status identifies that an electrode connection impedance test sequence is being carried out by the transmitter, that the test or call buttons have been pressed, or that telemetry transmitter 10 is in a low battery condition.

Upon the transmission of the four data frames noted above, the transmission sequence is repeated to transmit four additional data frames. The transmission sequence is thus repeated every 32 ms.

As noted in the simplified data table, above, the second and fourth data samples in each frame are described as "inverted." That is, the digital bits forming the nine data bytes of those samples are changed from one state to the other, opposite state. The reason for doing this is as follows.

When the stream of digital data comprising the modulating signal in conductor 74 contains large numbers of bits of only one signal state or large numbers of bits of only the other digital signal state, it causes the modulating signal to have low frequency characteristics. Such a data signal may be said to be "stationary" or possess "stationarity." This circumstance is in contrast to a typical digital data stream in which the digital data changes frequently between signal states and has approximately equal numbers of signals of each state so that a modulating digital signal formed therefrom has higher frequency characteristics. As noted below in connection with the description of the rf section of telemetry transmitter 10, higher frequency signals are less likely to be subject to degradation than lower frequency signals as a result of the response characteristics of phase locked loop 72.

To avoid degradation of the EKG modulating signal in the rf section, microprocessor 400 and parallel/series digital data converter 406 operate to transmit the four data samples in each data frame such that the data samples in each data frame alternate between a non-inverted and an inverted condition, as shown in the above table. By "non-inverted" it is meant that the bits of a data sample will each be of a designated binary state. By "inverted" it is meant that each bit of the data sample is changed to the opposite binary state.

This alteration between the non-inverted and inverted conditions will cause the data signal to have approximately equal number of bits in each signal state over an appropriate time interval, even when the data signal is stationary, so that the frequency of the digital data is higher and degradation of the transmitted data is avoided.

As will be noted from the simplified data structure for the data frames described above, the Barker data in the first data frame is also inverted. This inverted Barker data provides a flag or identifier to receiver 14 that enables the telemetry system to ascertain the beginning of a repetitive sequence of four frames of data in the serial data stream.

Should the signal transmitted by telemetry transmitter 10 become weak, the probability that errors will be present in the signal received by receiver 14, due to noise, increases. To reduce or correct for such errors, microprocessor 400 associates an error correction byte with each data sample of eight electrocardiographic data bytes. The error correction obtained by the error correction byte is predicated on the following observations. First, for EKG signals, magnitudinal changes are temporally consistent in all EKG channels. Thus, when large changes occur in the electrocardiographic data, they occur simultaneously in all channels, as for example, due to the contraction of the heart muscle. Second, the magnitudinal properties of the EKG signals in each of the channels are roughly the same. The foregoing is not true with respect to noise.

Based on the foregoing observations, an error correction byte provided in each data sample. This error correction byte is used by the receiver to limit the maximum change, or "max delta", between two successive samples of received EKG data in any of the channels to the maximum signal change occurring in any one of the EKG data channels. Any signal change found in the data in any of the EKG channels beyond that maximum signal change is deemed to be the result of noise or other spurious signals occurring during transmission of the data from telemetry transmitter 10 to receiver 14 and not as a result of the electrocardiographic data acquired by telemetry transmitter 10.

Microprocessor 400 thus obtains the magnitudes of the EKG signal data in a current data sample from each of the EKG channels. It also obtains the magnitude of EKG signal data in a previous data sample from each of the EKG channels. It examines the change or "delta" between the current and previous samples in each of the channels. The largest amount of change that is detected becomes the "max delta" quantity that comprises the error correction byte in the data transmitted to receiver 14.

Upon receipt of a data sample by receiver 14, the receiver determines the amount of change represented by the "max data" of the error correction byte. It also ascertains the actual change in the EKG signal data in each of the EKG channels. If the change in the EKG data between successive previous and current data samples in a given EKG channel is less than that represented by "max delta", the receiver accepts and processes the current signal data at its current magnitude as the data for that sample. If the change in the EKG data between previous and current samples in a given EKG channel is greater than that represented by "max delta", the receiver accepts and processes data comprising the previous data magnitude plus the amount of change represented by "max delta." The actual current signal data which is changed from the previous data by an amount in excess of that represented by "max delta" is deemed erroneous.

Thus, for example, if the maximum signal change between two successive samples of the electrocardiographic data acquired by telemetry transmitter 10 from the patient in any of the electrocardiographic data channels is represented by a change of two bits in the electrocardiographic data, the error correction or "max delta" byte in the transmitted data is used by receiver 14 to limit the maximum change between two successive samples in the received data signal for any of the channels to that represented by two bits. Any signal change beyond a two bit signal change is deemed to be the result of error or other spurious signals occurring during transmission. Should the maximum signal change between successive data samples of the acquired EKG data in any of the EKG channels be found to be four bits, the error correction byte instructs the receiver 14 that the maximum change between successive samples that the receiver can accept in any of the channels is now that represented by four bits.

It is recognized that there is the possibility that noise may appear in the data comprising the error correction or max delta byte. However, this will occur, at greatest in only 1/9 of the data since the error correction byte is only one of nine bytes being transmitted. In eight times out of nine the errors will appear in one of the data channels and may be corrected for by the valid information in the max delta, error correction byte. Further, if there is an error in the max delta data that indicates that a major change has occurred when, in fact, no major changes are found in any of the EKG channels, the error in the max delta byte is of no consequence.

The only circumstances under which error correction is ineffective is when an error in the max delta data indicates only a small change in the EKG data has occurred when, in fact, a large change in the EKG data has occurred. This has a very low relative probability of occurrence due to the characteristics of EKG data.

As noted above, each of the EKG data signal samples in the signal transmitted by transmitter 10 comprises an eight bit data byte. With eight bits of data for the EKG data signals, there is a limit to the amount of change that can be represented by the eight bits. In normal operation of telemetry transmitter 10 of the present invention, the least significant data bit in the EKG sample data bytes represents a signal of 2.5 microvolts. That is, a change in the binary state of the least significant bit represents a change in the analog EKG signal of 2.5 microvolts. This means that the maximum change that can be represented by the eight bits of a sampled EKG data byte in each channel is $2^8 \times 2.5$ microvolts or $256 \times 2.5$ microvolts or $-320$ to $+320$ microvolts. While this provides good resolution to a telemetry system incorporating telemetry transmitter 10, it is a rather small dynamic range when compared to that encountered with typical electrocardiographic data acquired from patients.

To overcome this problem, when the error correction byte in a sample unit of data frame is at its maximum digital value, the incremental magnitudinal change represented by the least significant bit in the transmitted EKG sample data is changed by a factor of four to 10 microvolts. This expands the dynamic range of the telemetry system to $-1,280$ to $+1,280$ microvolts. A maximum, max delta data byte condition in the transmitted data is used by receiver 14 to change its resolution from 2.5 microvolts/bit to 10 microvolts/bit.

As noted above in connection with the analog/digital converter portions of telemetry transmitter 10, the digital output of the analog/digital converter will usually consist of a digital word having a greater number of bits than the eight bit EKG data byte employed in the output of microprocessor 400 to conductor 74. Microprocessor 400 selects a segment of the larger digital word to comprise the eight bit EKG data byte. When the error correction data byte is below its maximum digital value, a certain segment of eight bits is selected from the larger digital word as the EKG data byte. When the error correction data byte is at its maximum digital value, the selected eight bit segment is shifted two bits in the larger digital word in the direction of the most significant bit. This increases the value of the least significant bit in the eight bit EKG data byte by the factor of four noted above. A rough analogy in the decimal system would be a shift from data showing 10.00 to data showing 1000.

The foregoing change in resolution expands the dynamic range of the telemetry transmitter. It also provides a high advantageous data compression to the transmitted EKG data since it enables the transmission of eight bits to contain ten bits worth of data due to the shifting occurring during a change of resolution.

It is to be noted that the error correction byte thus serves two function—error correction and data compression. Since one error correction byte in a data frame carries out both functions for the data samples for all eight EKG channels in the frame, the foregoing functions are obtained in a highly efficient manner, thereby facilitating the operation of telemetry transmitter 10.

When the error correction byte is at its maximum value, the error correction provided by the error correction byte is lost. However, the probability of error occurring with these conditions is lower because of infrequent occurrence of these conditions in the EKG signals. The telemetry system will revert to the 2.5 microvolt/bit resolution and restore error correction, when the changes in the data in all of the EKG channels is less than that represented by the maximum value of the error correction byte.

Even with the expanded scale of the telemetry system, it will be appreciated that there may still be occurrences in which changes in successive samples of the acquired EKG data exceed that which can be represented by an 8-bit byte. This maximum amount of incremental change may be termed the transmitted data "slew rate." Thus, if the EKG signal changed by 9 millivolts, as, for example, when a sudden, large DC offset voltage appears in the EKG data, it would take seven successive data samples for this 9 millivolt change to be reflected in the data transmitted to receiver 14 since the data outputted by microprocessor circuit 66 can change by a maximum of 1,280 microvolts, or 1.28 millivolts, per sample. However, any discrepancies in the data received at receiver 14 are well within the limits specified by various industry standards or regulatory authorities for monitoring and diagnostic electrocardiographic data.

The table below shows the specific data format used for the four data frames comprising one cycle of data transmission.

| BYTE | FUNCTION |
|---|---|
| 1 | INVERTED BARKER UPPER |
| 2 | INVERTED BARKER LOWER |
| 3 | PROGRAM NUMBER |
| 4 | HIGH SPEED STATUS |
| 5 | MAX DELTA (SAMPLE #1A) |
| 6 | LA-LL |
| 7 | LL |
| 8 | V1 |
| 9 | V2 |
| 10 | V3 |
| 11 | V4 |
| 12 | V5 |
| 13 | V6 |
| 14 | INVERTED MAX DELTA (SAMPLE #2A) |
| 15 | INVERTED LA-LL |
| 16 | INVERTED LL |
| 17 | INVERTED V1 |
| 18 | INVERTED V2 |
| 19 | INVERTED V3 |
| 20 | INVERTED V4 |
| 21 | INVERTED V5 |
| 22 | INVERTED V6 |
| 23 | MAX DELTA (SAMPLE #3A) |
| 24 | LA-LL |
| 25 | LL |
| 26 | V1 |
| 27 | V2 |
| 28 | V3 |
| 29 | V4 |
| 30 | V5 |
| 31 | V6 |
| 32 | INVERTED MAX DELTA (SAMPLE #4A) |
| 33 | INVERTED LA-LL |
| 34 | INVERTED LL |
| 35 | INVERTED V1 |
| 36 | INVERTED V2 |
| 37 | INVERTED V3 |
| 38 | INVERTED V4 |

-continued

| BYTE | FUNCTION |
|---|---|
| 39 | INVERTED V5 |
| 40 | INVERTED V6 |
| 41 | BARKER UPPER |
| 42 | BARKER LOWER |
| 43 | CHANNEL NUMBER |
| 44 | HIGH SPEED STATUS |
| 45 | MAX DELTA (SAMPLE #1B) |
| 46 | LA-LL |
| 47 | LL |
| 48 | V1 |
| 49 | V2 |
| 50 | V3 |
| 51 | V4 |
| 52 | V5 |
| 53 | V6 |
| 54 | INVERTED MAX DELTA (SAMPLE #2B) |
| 55 | INVERTED LA-LL |
| 56 | INVERTED LL |
| 57 | INVERTED V1 |
| 58 | INVERTED V2 |
| 59 | INVERTED V3 |
| 60 | INVERTED V4 |
| 61 | INVERTED V5 |
| 62 | INVERTED V6 |
| 63 | MAX DELTA (SAMPLE #3B) |
| 64 | LA-LL |
| 65 | LL |
| 66 | V1 |
| 67 | V2 |
| 68 | V3 |
| 69 | V4 |
| 70 | V5 |
| 71 | V6 |
| 72 | INVERTED MAX DELTA (SAMPLE #4B) |
| 73 | INVERTED LA-LL |
| 74 | INVERTED LL |
| 75 | INVERTED V1 |
| 76 | INVERTED V2 |
| 77 | INVERTED V3 |
| 78 | INVERTED V4 |
| 79 | INVERTED V5 |
| 80 | INVERTED V6 |
| 81 | BARKER UPPER |
| 82 | BARKER LOWER |
| 83 | LEAD FAIL |
| 84 | HIGH SPEED STATUS |
| 85 | MAX DELTA (SAMPLE #1C) |
| 86 | LA-LL |
| 87 | LL |
| 88 | V1 |
| 89 | V2 |
| 90 | V3 |
| 91 | v4 |
| 92 | V5 |
| 93 | V6 |
| 94 | INVERTED MAX DELTA (SAMPLE #2C) |
| 95 | INVERTED LA-LL |
| 96 | INVERTED LL |
| 97 | INVERTED V1 |
| 98 | INVERTED V2 |
| 99 | INVERTED V3 |
| 100 | INVERTED V4 |
| 101 | INVERTED V5 |
| 102 | INVERTED V6 |
| 103 | MAX DELTA (SAMPLE #3C) |
| 104 | LA-LL |
| 105 | LL |
| 106 | V1 |
| 107 | V2 |
| 108 | V3 |
| 109 | V4 |
| 110 | V5 |
| 111 | V6 |
| 112 | INVERTED MAX DELTA (SAMPLE #4C) |
| 113 | INVERTED LA-LL |
| 114 | INVERTED LL |
| 115 | INVERTED V1 |
| 116 | INVERTED V2 |

-continued

| BYTE | FUNCTION |
| --- | --- |
| 117 | INVERTED V3 |
| 118 | INVERTED V4 |
| 119 | INVERTED V5 |
| 120 | INVERTED V6 |
| 121 | BARKER UPPER |
| 122 | BARKER LOWER |
| 123 | LOW SPEED STATUS |
| 124 | HIGH SPEED STATUS |
| 125 | MAX DELTA (SAMPLE #1D) |
| 126 | LA-LL |
| 127 | LL |
| 128 | V1 |
| 129 | V2 |
| 130 | V3 |
| 131 | V4 |
| 132 | V5 |
| 133 | V6 |
| 134 | INVERTED MAX DELTA (SAMPLE #2D) |
| 135 | INVERTED LA-LL |
| 136 | INVERTED LL |
| 137 | INVERTED V1 |
| 138 | INVERTED V2 |
| 139 | INVERTED V3 |
| 140 | INVERTED V4 |
| 141 | INVERTED V5 |
| 142 | INVERTED V6 |
| 143 | MAX DELTA (SAMPLE #3D) |
| 144 | LA-LL |
| 145 | LL |
| 146 | V1 |
| 147 | V2 |
| 148 | V3 |
| 149 | V4 |
| 150 | V5 |
| 151 | V6 |
| 152 | INVERTED MAX DELTA (SAMPLE #4D) |
| 153 | INVERTED LA-LL |
| 154 | INVERTED LL |
| 155 | INVERTED V1 |
| 156 | INVERTED V2 |
| 157 | INVERTED V3 |
| 158 | INVERTED V4 |
| 159 | INVERTED V5 |
| 160 | INVERTED V6 |

Other functions performed by microprocessor 400 are as follows. Microprocessor 400 receives input signals from frequency set switches 48, 50 and employs the hexadecimal input signals therefrom to provide an output signal in bus 70 to phase locked loop 72 so that the latter, in turn, provides an output signal in conductor 80 that establishes the frequency of voltage controlled oscillator 78, and hence the desired center frequency of the rf carrier signal of telemetry transmitter 10.

Microprocessor 30 also receives input signals from test button 30 and call button 32 located on the front face of housing 22 of telemetry transmitter 10. In response to the condition of these buttons, microprocessor 400 initiates the calling function or the electrode impedance test sequence, described above, to alert medical personnel or to determine and display the impedance of each of the electrode connections in bar graph 34 of display module 28. For this purpose, microprocessor 400 provides a signal in data bus 408 to LCD driver 410. Liquid crystal display module 28 has a series of liquid crystal display segments which, when activated, make visible bar graph 34, torso 36, electrode location 37, and the alphabetical or numeric legends in display module 28. Display module 28 has an edge connector for each of the segments in the display. LCD driver 410 is operated by microprocessor 400 provide the appropriate signals in bus 411 to the edge connectors to create the desired visual image in the display module.

FIG. 9 is a flow chart showing the operation of microprocessor 400. The first step S1 in the operation of microprocessor 400 is to initialize the various circuities of telemetry transmitter 10. Thereafter, in step S2, microprocessor 400 looks for an interrupt signal, such as that provided by conductor 230 from the analog/digital converter 62 shown in FIG. 7. As noted above, during the short period when analog/digital converter 62 is outputting data on bus 64, an interrupt signal is provided to microprocessor 400 to block its operation while the analog/digital converter is using the data bus. Such a interrupt signal may be provided for approximately 20 microseconds every 20 ms. When no such signal is present, microprocessor 400 may output data to buffer 402, LCD driver 410, and phase locked loop 72. The output to buffer 402 is provided through parallel/series digital data converter 406 to conductor 74 to modulate the rf carrier signal of telemetry transmitter 10, as in step S3.

Thereafter, in step S4, microprocessor 400 loads electrocardiographic signal data from the analog/digital converter or from buffer 234.

In step S5, microprocessor 400 determines from the outputs of amplifiers 200 whether an electrode connection to the patient has been lost. As noted in connection with the description of input circuit 61, a high voltage signal at the output of one or more of amplifiers 200 is indicative of a lost electrode connection. Microprocessor 400 looks at the outputs of the amplifier 200 in each EKG data channel and, particularly at the most significant bits in the digital data corresponding to such outputs. These bits indicate signals of large magnitude. A digital data signal in excess of a certain threshold, for example greater than 350 millivolts, is indicative of an electrode fault.

If a lost electrode connection is found, a signal indicative of same is incorporated in the transmitted data, as for example in the third byte of the third data frame. A signal is also sent via bus 408 and LCD driver 410 to display module 28 to provide the visual indication shown in FIG. 2 and described above.

In step S6, the presence of a pacemaker spike in the EKG data is detected. This may be accomplished by use of the signal in conductor 216 in the embodiment of the invention shown in FIG. 5. Or, in the embodiment of the invention shown in FIG. 7, microprocessor 400 determines that the slew rate limit circuit in analog/digital converter 222 is in the limit condition and uses this condition as an indication of the presence of a pacemaker spike. Microprocessor 400 then alters the high speed status byte of each data frame in accordance with its determination. Each channel of EKG data is examined for the presence of pacemaker spikes.

In step S7, the digital state for the error correction or "max delta" byte in each data sample is established, in the manner described above, and provided to each of the data samples.

In step S8, if the error correction byte is in a condition indicative of the maximum data change that can be represented by the size of the digital word used for the EKG signal data, the resolution of the transmitted data is changed from, for example, 2.5 microvolts/bit to 10 microvolts/bit.

In step S9 microprocessor 400 provides output data in bus 70 to phase locked loop 72 to establish the frequency of the carrier signal. Data is also provided in bus 408 to LCD driver 410 to cause any necessary images to appear in display module 28.

If step S10 is initiated by operation of test button 30, microprocessor 400 initiates a test of the impedance of the electrodes, as described above in connection with the operation of input circuitry 61. Under normal circumstances, no impedance check is carried out so that the operation of microprocessor 400 is repeated in the next cycle. Steps S2 through S10 are carried out in a time period of less than 2 milliseconds, i.e. within the interval between interrupt signals in conductor 230 of analog/digital converter 62.

When the impedance of the electrodes is to be checked, step S10 carries out the test sequence shown in FIG. 6b for the circuitry shown in FIG. 6a used to determine the impedance of the electrodes. Microprocessor 400 also provides the data required by display driver 410 to provide the necessary graphic display in bar 34 of display module 28.

RF Section

Figure 10:
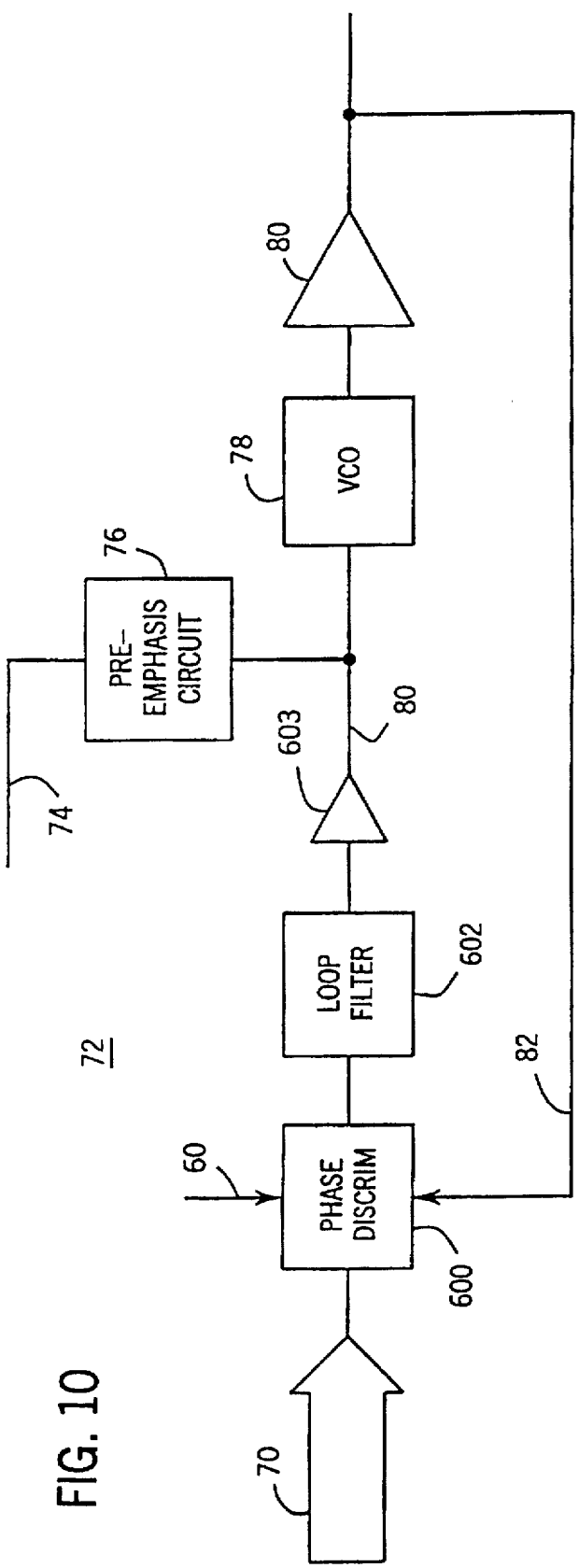
FIG. 10 is a schematic diagram of the phase locked loop and rf portions of the circuitry shown in FIG. 4.

FIG. 10 shows a detailed schematic diagram of the rf section of telemetry transmitter 10.

The rf section of telemetry transmitter 10 includes phase locked loop circuit 72 which provides a signal to the input of voltage controlled oscillator 78 in conductor 80 to establish the rf carrier frequency for telemetry transmitter 10. The modulating signal in conductor 74 is also provided to the voltage controlled oscillator. The output of voltage controlled oscillator 78 forms the input to radio frequency amplifier 80. The output of radio frequency amplifier 80 is provided as a feedback signal in conductor 82 to phase locked loop circuit 72. The output of radio frequency amplifier 80 is also provided through band pass filter 84 to antenna 23.

The phase locked loop 72 includes phase discriminator circuit 600 and loop filter 602. Phase discriminator circuit 600 receives as a reference or control signal, the output from control circuit 66 in bus 70 that establishes the desired operating frequency of the phase locked loop. Phase discriminator circuit 600 receives, as a feedback signal, the output of radio frequency amplifier 80 in conductor 82. Phase discriminator circuit 600 also receives the signal from clock circuit 58 in conductor 60 that provides a stable reference for the operation of the phase locked loop. Responsive to the reference and feed back signals, phase discriminator circuit 600 controls voltage controlled oscillator 78 so as to operate at a constant phase relative to the reference signal in bus 70. The phase, and hence the frequency, of the phase locked loop becomes locked to the frequency established by the signal in bus 70 from microprocessor 400 to an accuracy of approximately ±1 KHz. Phase discriminator 600 may be that component made and sold by National Semiconductor Corp., under the designation LMX1501.

Loop filter 602 provides an analog voltage signal suitable for operating voltage controlled oscillator 78, as well as compensation necessary to stabilize the operation of phase locked loop 72. Filter 602 may employ resistive and capacitance components. The output of loop filter 602 may be provided through isolating amplifier 603.

In a voltage controlled oscillator, such as oscillator 78, the frequency of the output signal of the oscillator is controlled by the voltage magnitude of the input signal thereto. The variation in the frequency of the output signal provided by a given voltage change applied to the input is termed the "sensitivity" of the voltage controlled oscillator and, for voltage controlled oscillator 78 would be expressed in MHz/volt.

Voltage controlled oscillator 78 may be that component manufactured and sold by Murata-Erie Corp. of Smyrna, Ga., under the designation MQE001-195. A voltage controlled oscillator 78 suitable for use in the telemetry system of the present invention may be one in which an input voltage in the range of 0–3 volts will vary the output frequency of the oscillator between 900 and 930 MHz.

The modulation signal from control circuit 66, provided in conductor 74, is applied to preemphasis circuit 76 and from preemphasis circuit 76 to the input of voltage controlled oscillator 78.

Figure 11:
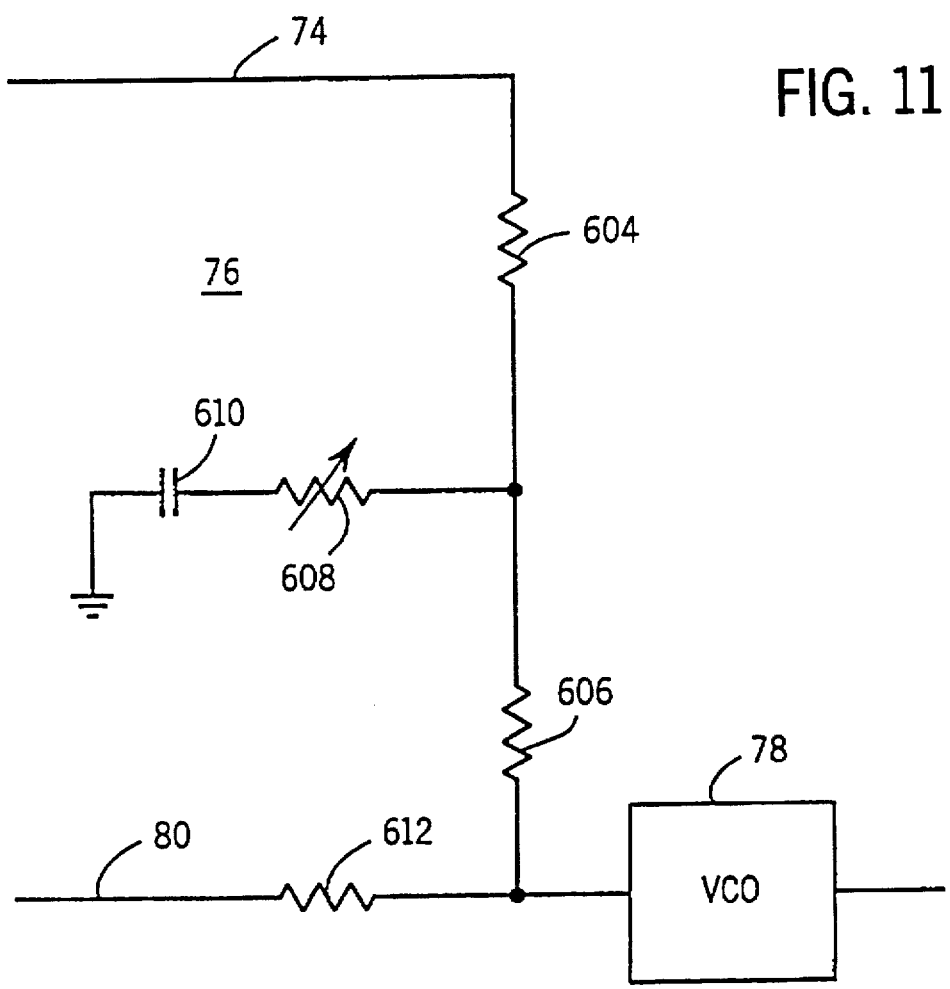
FIG. 11 is a detailed schematic diagram of a preemphasis circuit employed in the circuity shown in FIG. 10.

Preemphasis filter 76 is shown in detail, in FIG. 11. Preemphasis circuit 76 comprises series connected resistors 604 and 606. One end of variable resistor 608 is connected intermediate resistors 604 and 606. The other end of resistor 608 is connected through capacitor 610 to ground. Conductor 80 from the phase locked loop circuit 72 includes resistor 612.

The use of preemphasis circuit 76 is designed to overcome the foregoing problem heretofore encountered in connection with biomedical telemetry transmitter circuitry. When telemetry transmitter 10 is used, for example with an ambulatory patient, the position of antenna 23 will change, or the antenna touch the skin or the clothing of the patient, as the patient moves about. This causes the loading on the rf section of transmitter 10 to vary. The loading change is reflected to voltage control oscillator 78 and causes a change in the output frequency of the voltage controlled oscillator 78 and the frequency of the rf carrier signal of the transmitter. This phenomenon, termed "frequency pulling", is detrimental to the operation of the telemetry system.

To avoid frequency pulling, it is therefore desirable that the rf section have a very low sensitivity to changes in loading. One way of achieving this is to buffer the output of voltage controlled oscillator 78, i.e. provide isolation between voltage controlled oscillator 78 and antenna 23. This isolation is typically provided by attenuating the output of voltage controlled oscillator 78. However, such attenuation must be overcome by increasing the amplification provided by rf amplifier 80, which, in turn, increases the power consumption of transmitter 10 and increases the drain on batteries 40. Also, as the frequency of the rf carrier signal is increased, rf isolation becomes harder to achieve due to the input to output capacitance of rf amplifier 70.

Low sensitivity to loading changes could theoretically be carried out by increasing the response time, or bandwidth, of the phase locked loop so that it would regulate out frequency alterations of voltage controlled oscillator 78. However, increasing the response time of the phase locked loop tends to degrade the modulation of the carrier signal provided by the data signal in conductor 74 since variations in rf carrier signal frequency caused by the modulating signal also tend to get regulated out. The effect of this action is to reduce the amount of modulation of the carrier signal. This, correspondingly, provides an undesirable decrease in the signal to noise ratio of the telemetry system.

This reduction is particularly serious with respect to low frequency data in the modulating signal since a fast response time phase locked loop will more fully act to correct frequency alterations of the carrier signal caused by such data. In this connection, it must be appreciated that, while the signal in conductor 74 is a digital modulating signal comprised of a series of digital bits, the signal, nonetheless, has frequency properties depending on the exact sequence that the two binary states appear in the serial stream of data bits. For example, a digital signal that is continuously one or the other of the binary states represents a zero frequency. A digital signal that alternates between the two binary states represents a modulating digital signal of the highest frequency. Various sequence combinations of the two binary states in the modulating digital signal will yield frequencies between zero frequency and the highest frequency. It is therefore correct to speak of the varying frequency properties of the digital signal in conductor 74.

Another possibility for solving foregoing problem would be to increase the frequency of the modulating data signal in an effort to avoid the low frequency data signal loss noted above. Typical ways of doing this involve so called "Miller coding" or "Manchester coding" of the binary signal used to modulate the carrier signal.

However, increasing the frequency of the data signal requires an increase in the bandwidth of the transmitter in order to maintain the range of the transmitter, the maximum transmitting power of the transmitter being fixed by various regulatory authorities for safety reasons. With the increase in bandwidth comes increased noise injection in the signal which, again, results in an undesirable decrease in the signal to noise ratio. Increased bandwidth also decreases the utilization that can be made of a given radio frequency spectrum.

The rf section of transmitter 10 of the present invention overcomes the instabilities arising from frequency pulling by providing a phase locked loop 72 of increased response time, or increased bandwidth, and by employing preemphasis circuit 76 to provide a preemphasis or boost to the low frequency portions of the modulating data signal in conductor 74.

Figure 12A:
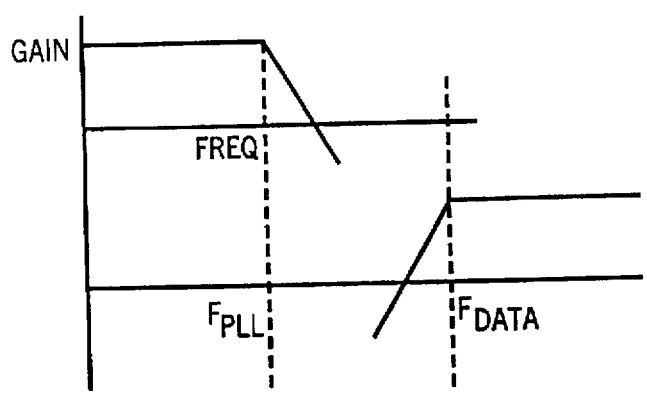
FIGS. 12a, 12b, and 12c show operating aspects of the circuit shown in FIG. 10.
Figure 12B:
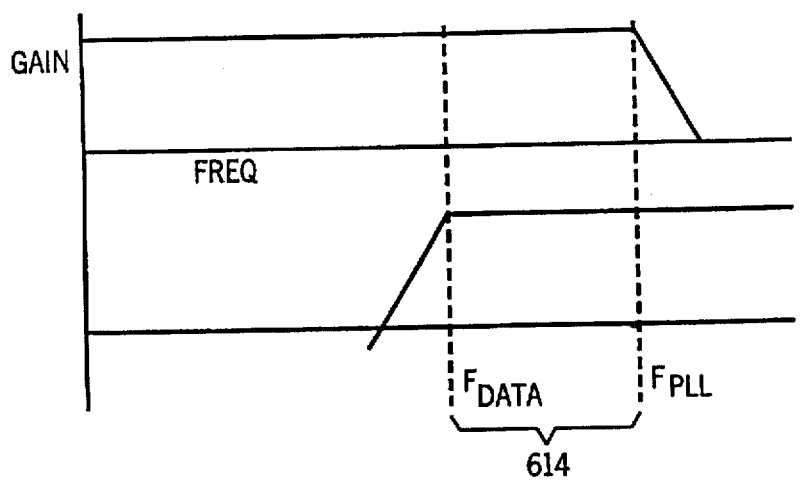
Figure 12C:
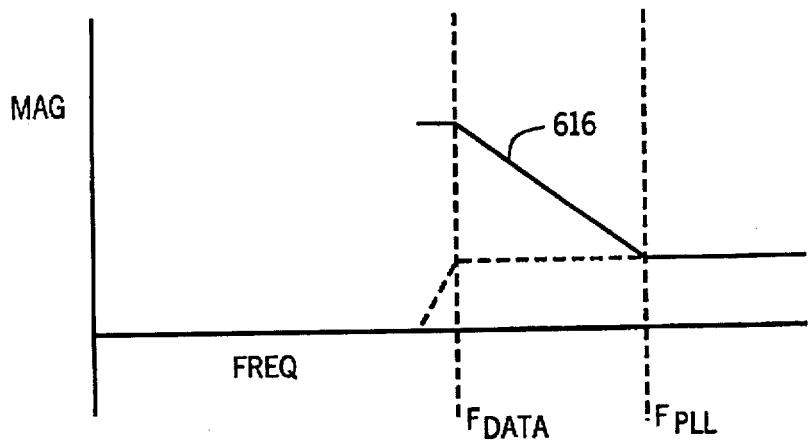

The manner in which the rf section of the present invention operates may best be seen by reference to the graphs of FIGS. 12a and 12b which show the bandwidth-frequency response characteristics of the rf section without expanded bandwidth (FIG. 12a) and with expanded bandwidth (FIG. 12b). FIG. 12c shows the low frequency boost provided by preemphasis circuit 76 of the present invention.

FIG. 12a shows the bandwidth characteristics of a conventional phase locked loop circuit, with the gain of the loop shown on the ordinate and the frequency of the loop shown on the abscissa.

The upper portion of FIG. 12a shows the bandwidth of the phase locked loop. The bandwidth of the phase locked loop is indicated on the abscissa of the graph by the distance between zero or some minimal operating frequency and the frequency $F_{PLL}$. Below the frequency $F_{PLL}$, the response time of the phase locked loop is such that the frequency of the phase locked loop can remain locked or regulated.

In the rf section of telemetry transmitter 10, the phase locked loop may have a time constant of 8 milliseconds. A time constant of 8 milliseconds corresponds to a bandwidth of 20 Hz.

With respect to the digital EKG modulating data signal, the lowest frequency condition of the modulating signal would be that in which the data is all of one binary state but alternates between the non-inverted and inverted conditions in the manner described above in connection with the description of the data frames of the serial data modulating signal. This inversion would provide a signal that alternates approximately every 2 milliseconds, i.e. the 8 ms time of a data frame divided by four data samples per frame. Attributing cyclical properties to the digital signal data would give it a period of 4 milliseconds and a frequency $F_{DATA}$ of approximately 250 Hz.

FIG. 12a shows an rf section in which the phase locked loop has a cut-off frequency $F_{PLL}$ or bandwidth of 20 Hz and the modulating digital data signal has a cut-off frequency $F_{DATA}$ of 250 Hz.

In a phase locked loop displaying bandwidth and corresponding response times shown in FIG. 12a, the frequency characteristics of the modulating data signal are sufficiently high that the response time of the phase locked loop does not effect the alteration of the rf carrier signal caused by the modulating signal. That is, the modulating data signal does not get regulated out. This enables full modulation of the carrier signal to occur and ensures information contained in the modulating signal is fully transmitted. However, the response time of the phase locked loop will be so slow that it cannot prevent alterations in carrier frequency resulting from frequency pulling. This detracts from the quality of operation of the telemetry system employing transmitter 10.

FIG. 12b shows a phase locked loop in which the bandwidth, and response time, has been increased in an effort to reduce degradation of the transmitting characteristics of the transmitter as a result of frequency pulling. For example, the bandwidth is increased from 20 Hz to 1 KHz to lessen or eliminate the effects of frequency pulling. This is accomplished by altering the resistive and capacitance components of loop filter 602. However, as can be seen from FIG. 12b, if the frequency response characteristics of the phase locked loop are increased, they then act to reduce or eliminate the modulation to the carrier signal provided by the modulating EKG data signal, and particularly the low frequency components thereof. That is, digital modulating EKG data signals in conductor 74 having a frequency falling in the range identified by the reference numeral 614 in FIG. 12b are now within the bandwidth of the phase locked loop and thus subject to its regulating action. The regulating action of the phase locked loop will prevent or lessen alteration of the frequency of the carrier signal caused by such data signals, thereby degrading the performance of transmitter 10.

FIG. 12c shows the preemphasis provided by preemphasis circuit 76. FIG. 12c is similar to FIG. 12b except that the ordinate indicates signal magnitude. As shown in FIG. 12c, preemphasis circuit 76 increases the magnitude of the digital EKG modulating signal 616 at frequencies less than the frequency $F_{PLL}$ forming the cutoff frequency for phase locked loop 72.

With the preemphasis to digital EKG modulating signals of low frequency in conductor 74, the degradation or decrease in the performance of transmitter 10 with respect to signals of such frequency is lessened or overcome. This is due to the fact that the larger magnitude low frequency digital modulating signals will call for a larger variation in the frequency of the rf carrier signal at the output of voltage controlled oscillator 78. While the regulating action of phase locked loop 72 will act to reduce such frequency variation, the initially larger variation means that the amount of frequency variation remaining after the regulating action of phase locked loop 72 is sufficient to ensure the quality of the data being transmitted by transmitter 10. The degradation in the quality of the data being transmitted by transmitter 10 as a result of frequency pulling is thus reduced or eliminated in the telemetry transmitter 10 of the present invention.

The amount of preemphasis provided by preemphasis circuit 76 may be controlled by adjusting the magnitude of resistor 608.

The use of preemphasis circuit 76 provides an additional feature to the rf section of telemetry transmitter 10. As noted above, one of the operating characteristics of voltage controlled oscillator 78 is its sensitivity: that is, the amount of output frequency variation provided by a given input voltage variation. However, in practice, the sensitivity of a voltage controlled oscillator will vary from component to component due to manufacturing variations and tolerances and for other reasons. The variation in the sensitivity of the voltage controlled oscillator has an adverse impact on the stability of the rf section of the transmitter.

Variations in the sensitivity of voltage controlled oscillator 78 employed in the rf section of transmitter 10 may be compensated for by adjustment of variable resistor 608 used to establish the amount of preemphasis. Further, it has been additionally found that the value of resistor 608 that provides the necessary compensation to voltage controlled oscillator 76 also provides the appropriate amount of preemphasis to the digital modulating EKG signal data contained in conductor 74. That is, when resistor 608 is adjusted to provide the desired compensation to voltage controlled oscillator 78, the desired preemphasis characteristics are also provided to the modulating signal.

For example, in circumstances in which voltage controlled oscillator 78 has greater than normal sensitivity, this increased sensitivity causes the bandwidth of phase locked loop 72 to increase causing a mismatch between the cut-off frequency $F_{PLL}$ and the frequency at which preemphasis commences. Similarly, it causes the amount of frequency deviation in the transmitted signal resulting from the signal in conductor 74 to voltage controlled oscillator 78 to increase. This is undesirable since it may expand the operation of telemetry transmitter 10 beyond its bandwidth into other transmitter channels. By reducing the magnitude of resistor 608, the magnitude of the modulating signal to voltage controlled oscillator 78 is decreased. This causes the amount of frequency deviation to decrease. Decreasing the resistance of resistor 608 will cause the frequency at which preemphasis of the modulating signal commences to increase. This will cause it to match the new cut-off frequency $F_{PLL}$ resulting from the greater than normal sensitivity of the voltage controlled oscillator.

The Telemetry Receiver

Figure 13:
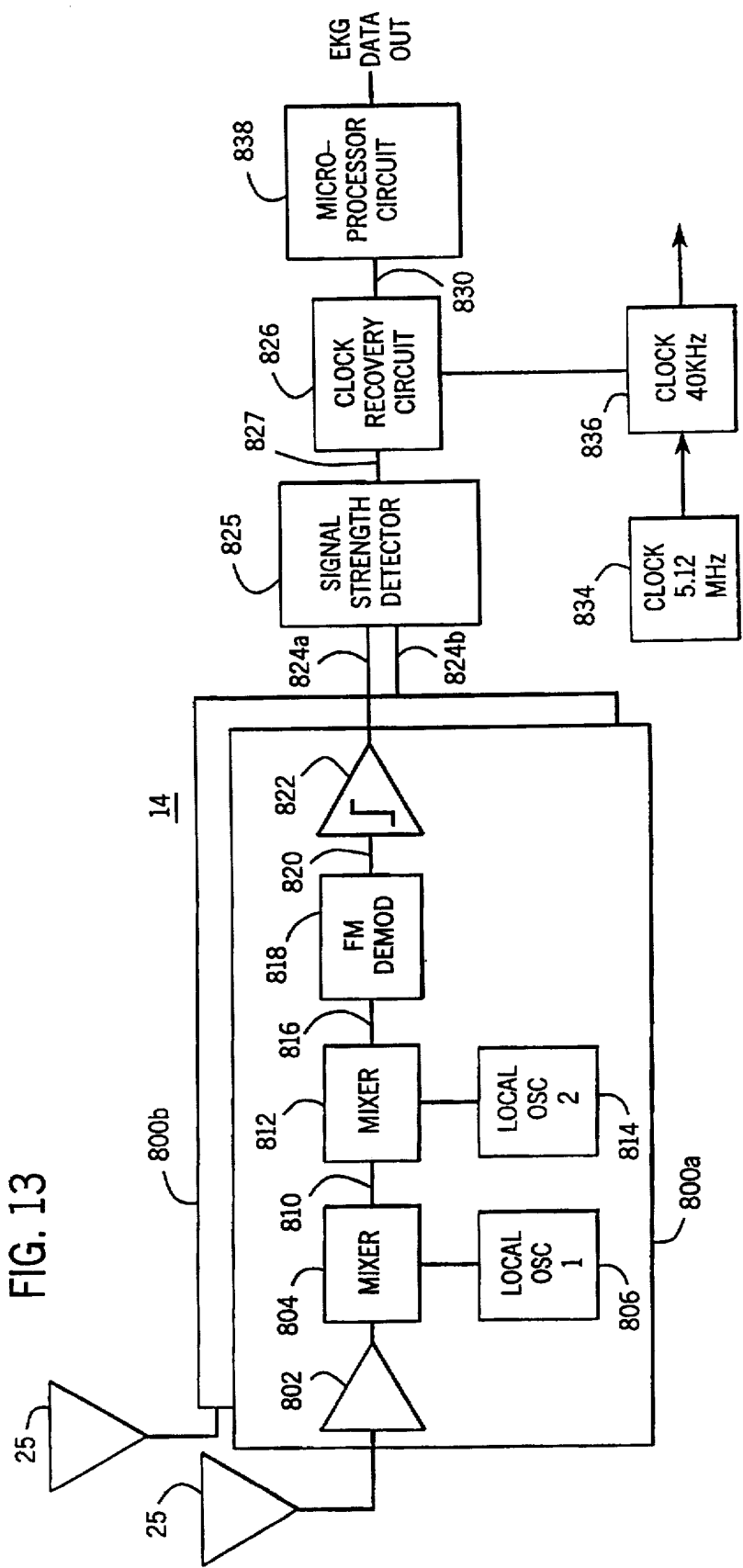
FIG. 13 is a general schematic diagram of a receiver suitable for use with the transmitter of the present invention.

FIG. 13 shows, generally, a telemetry receiver 14 suitable for use with telemetry transmitter 10 of the present invention. The output from antenna 23 of telemetry transmitter 10 is received at receiver antennae 25. Receiver 14 may be of the diversity type having a pair of antennae to overcome signal drop out resulting from the location or position of transmitter 10. Each of antennae 25 is connected to one of input circuits 800a, 800b. Input circuit 800a is shown in detail in FIG. 13.

The rf signal received at antennae 25 is provided through rf amplifier 802 to a first mixer 804 driven by first local oscillator 806. Local oscillator 806 may, for example, provide a signal equal to the carrier frequency of the rf signal of telemetry transmitter 10 plus 58.7 MHz. By the mixing or heterodyning action carried out in mixer 804, the signal from amplifier 802 and the signal from local oscillator 806 produce an output signal having a frequency equal to the difference between the frequency of the rf carrier signal of telemetry transmitter 10 and that of local oscillator 806, or in the example used above, a signal having a frequency of 58.7 MHz. This signal is provided in conductor 810. The signal in conductor 810 is subjected to a further heterodyning action in mixer 812 connected to local oscillator 814 to produce a signal having, for example, a frequency of 10.7 MHz.

The output signal of mixer 812 in conductor 816 is provided to fm demodulator 818. Demodulator 818 recovers the received counterpart of the digital modulating EKG signal data in conductor 74 of telemetry transmitter 10. To obtain an improved quality digital signal for further processing in receiver 14, the output of demodulator 818 is provided to a comparator 822 that converts the output signal in conductor 824 into one suitable for forming a digital signal.

The outputs of input circuits 800a and 800b in conductors 824a and 824b are provided to signal strength detector 825 that selects the output of circuit 800a or 800b having the greatest magnitude for use by the remaining portion of receiver 14.

The output of signal strength detector 825 in conductor 827 is provided to clock recovery circuit 826. Clock recovery circuit 826 formats the received signal so that the remaining portions of receiver 14 characterize it as a digital signal having bit increments. Clock recovery may be obtained by oversampling the output of comparator 822. Receiver 14 may be provided with the necessary clock circuit 836, 834 required for clock recovery.

The signal from clock recovery circuit 826 is provided to microprocessor circuit 828 in conductor 830. Microprocessor circuit 828 processes the digital data in the received signal and provides an output signal comprising the magnitude of the electrocardiographic signal in each of the eight EKG data channels. Such a signal is usually provided in digital form for storage in digital magnetic storage means or to drive a digitally operated graphic display device that, for example, provides a tracing of the electrocardiographic data on a moving paper strip. If analog EKG signals are desired, the digital data is provided to a digital/analog converter to provide same.

We claim:

1. A biomedical telemetry transmitter suitable for transmitting data from a plurality of biomedical data signals originating as analog input signals produced by biomedical sensors, said telemetry transmitter comprising:

an input circuit for receiving the analog input signals and providing the biomedical data signals;

an analog/digital converter for converting the biomedical data signals to corresponding digital signals;

control means coupled to said analog/digital converter for receiving said digital signals, said control means including means for providing a serial digital modulating signal from the digital signals of said analog/digital converter and for introducing data compression in the provision of said digital modulating signal;

an rf signal generating means for generating an rf carrier signal; and means coupled to said control means and to said rf signal generating means for frequency modulating the rf carrier signal with said digital modulating signal to form a transmission signal for said transmitter containing data from said plurality of biomedical data signals.

2. A biomedical telemetry transmitter according to claim 1 wherein said control means is further defined as including means establishing a resolution for the digital modulating signal and wherein said control means includes means for altering the resolution of the digital modulating signal, thereby to achieve data compression.

3. A biomedical telemetry transmitter according to claim 2 wherein said analog/digital converter includes means for sampling the analog input signals at sampling intervals, wherein said control means includes means for determining the maximum signal change in the biomedical data signals between two successive signal samples, wherein said control means further includes means for providing error correction data in the digital modulating signal indicative of the maximum signal change occurring in any of the biomedical data signals for use in limiting the data change in any of the biomedical data signals to said maximum signal change, the error correction data having a maximum value, and wherein said altering means is further defined as altering the resolution of the digital modulating signal when the error correction data is in a maximum value condition.

4. A biomedical telemetry transmitter according to claim 2 wherein said control means receives digital signals from said analog/digital converter in the form of digital words having a given number of bits expressing the magnitude of the analog input signals, wherein said control means provides a digital modulating signal in which the magnitude of the biomedical data is expressed in digital words having a fewer number of bits and selected from said given number of bits, and wherein said altering means of said control means shifts the bits selected from the given number of bits that are used to form the digital words in the digital modulating signal to alter the resolution of the digital modulating signal.

5. A biomedical telemetry transmitter according to claim 4 wherein the biomedical data signals change in magnitude, and wherein said altering means alters the resolution of the digital modulating signal responsive to magnitudinal changes in a biomedical data signal.

6. A biomedical telemetry transmitter according to claim 4 wherein said control means comprises means selecting from said given number of bits, a fewer number of bits for forming digital words that are outputted by said control means; and said altering means comprises means for shifting the bits selected from the given number of bits used to form the digital words in the digital modulating signal in the direction of the most significant bit, thereby to alter the resolution of the digital modulating signal while achieving a data compression related to the number of bits by which the digital word of the signal is shifted.

7. A biomedical telemetry transmitter according to claim 6 wherein the magnitude of said digital modulating signal changes and wherein said altering means carries out bit shifting and alters the resolution of said digital modulating signal in response to digital modulating signal magnitude changes.

8. A biomedical telemetry transmitter according to claim 4 wherein said analog/digital converter includes means for sampling the analog input signals at sampling intervals, wherein said control means includes means for determining the maximum signal change in the biomedical data signals between two successive signal samples, wherein said control means further includes means for providing error correction data in the digital modulating signal indicative of the maximum signal change occurring in any of the biomedical data signals for use in limiting the data change in any of the biomedical data signals to said maximum signal change, the error correction data having a maximum value, and wherein said altering means is further defined as altering the resolution of the digital modulating signal when the error correction data is in a maximum value condition.

9. A biomedical telemetry transmitter according to claim 1 wherein said control means further includes means for forming a plurality of data frames, each of said data frames containing data from each of said plurality of biomedical data signals, and wherein said control means further includes means for repetitiously incorporating the data frames in the serial digital modulating signal.

10. A biomedical telemetry transmitter according to claim 1 wherein said analog/digital converter includes means for sampling the analog input signals at sampling intervals, wherein said control means includes means for determining the maximum signal change in the biomedical data signals between two successive signal samples, and wherein said control means further includes means for providing error correction data in the digital modulating signal indicative of the maximum signal change occurring in any of the biomedical data signals for use in limiting the data change in any of the biomedical data signals to said maximum signal change.

11. A biomedical telemetry transmitter according to claim 10 wherein said control means further includes means for forming a plurality of data frames, each of the data frames containing data from each of the plurality of biomedical data signals, wherein said control means further includes means for repetitiously incorporating data frames in the serial digital modulating signal, and wherein said means for providing error correction data incorporates error correction data in each of the data frames for use in limiting the data change in any of the biomedical data signals of the frame to said maximum change.

12. A biomedical telemetry transmitter according to claim 10 wherein the error correction data has a maximum value and wherein said control means is further defined as changing the resolution of the digital modulating signal when the error correction data is in a maximum value condition.

13. A biomedical telemetry transmitter according to claim 10 wherein a plurality of digital signals corresponding to biomedical data signals are successively provided to a receiver and wherein said control means provides error correction data in the form of a means by which the effects of spurious signals may be minimized in the plurality of digital signals transmitted to the receiver, the digital signals corresponding to the biomedical data signals and provided by said analog/digital converter having origins in a common signal source, said control means comprising:

means for determining the amount of change occurring between two successive digital signal samples of any one of said digital signals of the analog/digital converter; and means for associating with at least one of said digital signals, an indicator indicative of the amount of said change, said indicator comprising said spurious signal minimizing means and being usable by the receiver to limit the change in successively transmitted pluralities of said digital signals to that represented by said indicator.

14. A biomedical telemetry transmitter according to claim 13 wherein the resolution of the digital signals is changeable, wherein there is a limit to the amount of digital signal change that can be indicated by said indicator, wherein said control means is further defined as including means establishing a resolution for the digital modulating signal, wherein said control means includes means for altering the resolution of the digital modulating signal to achieve data compression and wherein when said indicator provides an indication indicative of the change limit condition, said altering means alters the resolution of the digital signal.

15. A biomedical telemetry transmitter according to claim 13 wherein said control means is further defined as forming said digital signals into a plurality of data frames, each of which contain data of said plurality of digital signals, and wherein said associating means incorporates an indicator in each of said data frames or use in limiting the data change of the received data in any of said digital signals of said frame.

16. A biomedical telemetry transmitter according to claim 13 wherein said biomedical telemetry transmitter is further defined as a biomedical telemetry transmitter for minimizing the effects of spurious signals in telemetrically transmitted digital EKG data signals.

17. A biomedical telemetry transmitter according to claim 1 wherein the digital modulating signal is formed of bits and wherein said control means is further defined as periodically inverting the bits of the digital modulating signal to avoid stationarity in the data of the digital modulating signal.

18. A biomedical telemetry transmitter according to claim 17 wherein the digital modulating signal is formed of a succession of digital bits capable of having one signal state or another signal state, said digital modulating signal being subject to a condition of stationarity in which the bits are of one signal state or the another signal state in a given period of time; said control means includes means for avoiding the condition of stationarity comprising:

means for dividing the digital modulating signal into sequential increments comprising at least one bit; and means for inverting the bits of selected ones of the increments of the digital modulating signal to avoid the condition of stationarity.

19. A biomedical telemetry transmitter according to claim 18 wherein said means for dividing the data signal into sequential increments is further defined as dividing the data signal into sequential increments comprising a plurality of data bits.

20. A biomedical telemetry transmitter according to claim 19 wherein said inverting means is further defined as inverting the bits of every other one of said sequential increments.

21. A biomedical telemetry transmitter according to claim 19 wherein said inverting means is further defined as carrying out the inversion of selected ones of the increments so as to create a desired frequency characteristic in the digital modulating signal.

22. A biomedical telemetry transmitter according to claim 1 wherein said transmitter has a transmitting antenna coupled to said rf signal generating means and wherein said transmitter is subject to instabilities as a result of changes in loading reflected from the antenna, wherein said rf signal generating means includes means for stabilizing said transmitter against such instabilities comprising: regulator means for establishing the frequency of the rf carrier signal; means for providing a predetermined regulating response time for said regulator means sufficient to maintain the established frequency of the rf carrier signal in the face of changes in reflected loading from the antenna, the response time providing a corresponding bandwidth to said rf signal generating means, the bandwidth being defined by a lower cutoff frequency and an upper cutoff frequency; wherein the digital modulating signal possesses frequency properties which lie in a frequency range having frequencies less than, and frequencies greater than, said bandwidth upper cutoff frequency, so that a portion of the frequency range lies within the bandwidth of the rf signal generating means; and wherein said rf signal generating means includes a preemphasis circuit for increasing the magnitude of the portion of digital modulating signal having frequencies less than the upper cutoff frequency of the bandwidth of the rf signal generating means.

23. A biomedical telemetry transmitter according to claim 1 wherein the biomedical sensors comprise electrodes connected to a patient and wherein said input circuit has means couplable to the electrodes for ascertaining the impedance of the connections of the electrodes to the patient.

24. A biomedical telemetry transmitter according to claim 23 wherein the connection of the electrodes to the patient gives rise to an electrical impedance and said telemetry transmitter includes a visual display unit coupled to said ascertaining means in said input circuit for providing a visual indication of the magnitude of the impedance of the connections of the electrodes to the patient.

25. A biomedical telemetry transmitter according to claim 1 wherein the plurality of biomedical data signals originate at a plurality of biomedical sensors connected to a patient and wherein said input circuit has means couplable to the biomedical sensors for ascertaining the loss of a sensor connection to the patient.

26. A biomedical telemetry transmitter according to claim 25 wherein the biomedical sensors are connected to the patient at predetermined positions on the body of the patient and wherein said telemetry transmitter includes a visual display means coupled to said ascertaining means for providing a visual indication of the position of a disconnected biomedical sensor on the body of the patient.

27. A biomedical telemetry transmitter according to claim 23 wherein said input circuit comprises:

a conductor having a terminal to which one of the biomedical sensors can be coupled;

a differential amplifier, said differential amplifier having one input connected to said conductor, said differential amplifier providing an output signal;

means providing a reference signal to another input of said differential amplifier;

a current source connected to said conductor intermediate said terminal and said one input of said amplifier, the loss of the connection of the one of the biomedical sensors to the patient causing said current source to generate a voltage at said one input; and means for measuring the change in the output of said differential amplifier responsive to the generation of the voltage at said one input for determining the loss of the sensor-patient connection and for providing an indication of same to said control means.

28. A biomedical telemetry transmitter according to claim 27 wherein said input circuit determines the impedance of a connection of the one of the biomedical sensors to the body of the patient, said input circuit further comprising means for altering the current produced by said current source, and wherein said measuring means is further defined as measuring the change in the output of said differential amplifier responsive to the alteration of the current from said current source for determining the impedance of the sensor-patient connection.

29. A biomedical telemetry transmitter according to claim 28 wherein said signal from the one of the biomedical sensors is subject to variation as a result of the physiological functioning of the patient, wherein said current altering means is further defined as means for periodically altering the current; wherein said measuring means is further defined as means for repetitiously measuring the output of said differential amplifier; and wherein said measuring means includes means for averaging repetitious measurements for lessening the effect of said variation in the determination of the sensor connection impedance.

30. A biomedical telemetry transmitter according to claim 28 wherein the biomedical sensors comprise electrocardiographic electrodes and wherein said input circuit is further defined as including means for determining the impedance of the connection of one of the electrocardiographic electrodes to the body of a patient.

31. A biomedical telemetry transmitter according to claim 27 wherein said input circuit has a second conductor having a second terminal to which a second sensor of said plurality of sensors can be coupled, said second conductor being connected to said another input of said differential amplifier for supplying the analog input signal of said second sensor to said another input of said differential amplifier, said input circuit further including means connected to said second conductor for causing said signal in said second conductor to form said reference signal to said another input of the differential amplifier.

32. A biomedical telemetry transmitter according to claim 31 wherein said input circuit is further defined as detecting the loss of connection of the second sensor from the body of the patient, and wherein said input circuit further comprises:

a second amplifier having a pair of inputs, said second conductor being connected to a third conductor for supplying the signal from said second sensor to one input of said second amplifier;

a reference source connected to the other input of said second amplifier;

a second current source connected to said second conductor intermediate said second terminal and the connection of said third conductor to said second conductor;

means for generating a voltage at said one input of said first amplifier upon the loss of the second sensor-patient connection; and wherein said measuring means is further defined as measuring the change in the output of said differential amplifier responsive to the generation of the voltage at said one input for determining the loss of said second sensor-patient connection.

33. A biomedical telemetry transmitter according to claim 32 wherein said input circuit is further defined as determining the impedance of the connection of the first and second sensors to the body of the patient, wherein said input circuit includes means for intermittently altering the current produced by said first current source or said second current source in a manner such that intervals exist when the current of one source is altered but the current of the other source is not altered, and wherein said measuring means is further defined as measuring the change in the outputs of said first differential amplifier and said second differential amplifier responsive to the alteration of the current from said first and second current sources for determining the impedance of the first sensor-patient connection and the second sensor-patient connection.

34. A biomedical telemetry transmitter according to claim 25 wherein the biomedical sensors comprise electrocardiographic electrodes and wherein said input circuit is further defined as including means for determining the loss of the connection of one of the electrocardiographic electrodes to the body of the patient.

35. A biomedical telemetry transmitter according to claim 1 wherein said analog/digital converter comprises an eight channel, 20-bit analog/digital converter sampling the analog input signals at a frequency of 10 KHz and providing a digital output having a frequency of 500 Hz.

36. A biomedical telemetry transmitter according to claim 1 wherein the plurality of biomedical data signals comprise EKG data signals containing pacemaker spikes, wherein said analog/digital converter includes means for sampling the biomedical data-signals at sampling intervals, wherein said analog/digital converter has a slew rate detector detecting change in the data signals between two successive signal samples, and wherein said slew rate detector detects said pacemaker spike signals from the data signal change in successive samples and provides a signal in accordance therewith to said control means.

37. A biomedical telemetry transmitter according to claim 1 wherein said control means is further defined as including means for providing a digital modulating signal having a data rate up to 40 Kilobits/second.

38. A biomedical telemetry transmitter according to claim 37 wherein said rf signal generating means is further defined as rf signal generating means having a 100 KHz bandwidth.

39. A biomedical telemetry transmitter according to claim 1 wherein the biomedical data signals are further defined as eight EKG signals, wherein said analog/digital converter is further defined as an analog/digital converter having a 500 Hz sampling rate, and wherein said control means is further defined as including means for providing a digital modulating signal having a 40 Kilobits/second data rate.

40. A biomedical telemetry transmitter according to claim 1 wherein the telemetry transmitter is further defined as a telemetry transmitter for transmitting a plurality of EKG data signals.

41. A biomedical telemetry transmitter according to claim 1 wherein said control means includes a microprocessor coupled to said input circuit and to said rf signal generating means.

42. A biomedical telemetry transmitter according to claim 1 wherein said rf signal generating means includes a phase locked loop coupled to said control means for generating the rf carrier signal.

43. A biomedical telemetry transmitter according to claim 1 wherein said transmitter has a transmitting antenna coupled to said rf signal generating means, wherein said rf signal generating means reduces frequency alteration of the rf carrier signal resulting from changes in antenna loading reflected to the rf signal generating means while maintaining the quality of the data modulation of the rf carrier signal, and wherein said rf carrier signal generating means includes an oscillator providing an rf carrier signal to the antenna, said oscillator being incorporated in a control loop having a frequency bandwidth within which said control loop acts to establish and maintain the frequency of the rf carrier signal, said oscillator receiving the digital modulating signal having a frequency characteristic extending over a range of frequencies, said rf signal generating means further including means for establishing the bandwidth of said control loop to a width such that the control loop can maintain the frequency of the rf carrier signal when the rf signal generating means is subjected to changes in reflected antenna loading, said bandwidth of said control loop, so established, overlapping a low frequency portion of the frequency range of the digital modulating signal; and preemphasis circuit means for increasing the magnitude of said low frequency portion of the digital modulating signal to maintain the modulation of the rf carrier signal.

44. A biomedical telemetry transmitter according to claim 43 wherein said preemphasis circuit means is further defined as means for providing an adjustable amount of magnitude increase to said low frequency portion of the digital modulating signal.

45. A biomedical telemetry transmitter according to claim 44 wherein said preemphasis circuit means includes an adjustable resistor for adjusting the amount of magnitude increase, wherein said oscillator exhibits a sensitivity between input signal magnitude and output frequency, and wherein said adjustable resistor is coupled to the input of said oscillator means for compensating said oscillator means for variations in sensitivity.

46. A biomedical telemetry transmitter according to claim 1 wherein the plurality of biomedical data signals originate at biomedical sensors comprising electrodes applied to the torso of a patient, and wherein said telemetry transmitter includes a display means for providing a display indicating the electrical condition of the electrodes, each of said electrodes having an identification and being applied at predetermined locations on the torso of the patient, the electrical condition of said electrodes being determined by said input circuit, said display means comprising:

means presenting a surface on which visibly discernible patterns may be formed;

means coupled to said surface means and operable to form a visibly discernible outline of a human torso in said surface;

means coupled to said surface means and operable to provide an indication, in said surface, of the location and identification of the electrodes on the torso outline representing the corresponding electrode identification and locations on the torso of the patient; and means coupled to said input circuit and to said indication means for operating said indication providing means to indicate the location and identification of an electrode having an electrical condition determined to be faulty by said input circuit.

* * * * *